United States Patent [19]
Howley et al.

[11] Patent Number: 5,821,048
[45] Date of Patent: Oct. 13, 1998

[54] METHODS, KITS, AND COMPOSITIONS FOR DIAGNOSING PAPILLOMAVIRUS INFECTION

[75] Inventors: Peter M. Howley, Wellesley; John D. Benson, Brookline; Toshiharu Yasugi, Brookline; Hiroyuki Sakai, Brookline, all of Mass.

[73] Assignee: President and Fellows of Harvard College, Cambridge, Mass.

[21] Appl. No.: 472,666

[22] Filed: Jun. 7, 1995

[51] Int. Cl.⁶ .................. C12Q 1/70; C12Q 1/68; A01N 37/18; C07K 1/00
[52] U.S. Cl. ................ 435/5; 435/6; 435/235.1; 514/2; 530/350
[58] Field of Search .................. 435/5, 235.1, 6; 530/350; 514/2

[56] References Cited

U.S. PATENT DOCUMENTS

| | | | |
|---|---|---|---|
| 4,833,080 | 5/1989 | Brent et al. | 435/172.3 |
| 5,219,990 | 6/1993 | Androphy et al. | 530/350 |

FOREIGN PATENT DOCUMENTS

| | | |
|---|---|---|
| 0 257 754 A2 | 3/1988 | European Pat. Off. . |
| WO 92/11290 | 7/1992 | WIPO . |
| WO 94/10300 | 5/1994 | WIPO . |

OTHER PUBLICATIONS

Thorner et al., *J. Virol.* (1993) 67: 6000–6014.
Frattini et al., *Virol.* (1994) 204: 799–804.
Chiang et al., *Proc. Natl. Acad. Sci. USA* (1992) 89: 5799–5803.
Bream et al., *J. Virol.* (1993) 67: 2655–2663.
Chiang et al., *J. Virol.* (1992) 66: 5224–5231.
Lusky et al., *Proc. Natl. Acad. Sci. USA* (1991) 88: 6363–6367.
Yang et al., *Cold Spring Harbor Symp. Quant. Biol.* (1991) 56: 335–346.
Gillette et al., *Proc. Natl. Acad. Sci. USA* (1994) 91: 8846–8850.
Yang et al., *Nature* (1991) 353:628–632.
Müller et al., *J. Biol. Chem.* (1994) 269: 17086–17094.
Le Moal et al., *J. Virol.* (1994) 68: 1085–1093.
Lusky et al., *Proc. Natl. Acad. Sci, USA* (1994) 91: 8895–8899.
Ustav et al., *Proc. Natl. Acad. Sci. USA* (1993) 90: 898–902.
Chiang et al., *J. Virol.* (1991) 65: 3317–3329.

*Primary Examiner*—Marian C. Knode
*Assistant Examiner*—Ali R. Salimi
*Attorney, Agent, or Firm*—Hale and Dorr LLP

[57] ABSTRACT

Methods, kits, and compositions are provided for diagnosing papillomavirus infections by detecting the interaction between a papillomavirus E1 protein interaction domain and a papillomavirus E2 protein interaction domain.

3 Claims, 5 Drawing Sheets

HPV-16 E2 PREY

E2(1-106aa)
E2(61-190aa)
E2(164-245aa)
E2(1-150aa)
E2(33-190aa)
E2(1-190aa)
E2(61-245aa)
E2(1-245aa)
E2(164-365aa)
E2(1-365aa)

HPV-16 E1 BAITS

```
           106                       116                126              136                 144
HPV16.E2   VS LEVYYLTA P        TGCIK K HGYT    VE Q FD GDIC   NTMHYTN WT H    I T ICE--EAS
BPV1.E2    TS WDRYMSE D         KRCFK K GARV    VE V EFD GNAS  NTNWYTVYSN      L Y MRT--EDG
HPV6b.E2   TS YEMWQTP P         KRCFK K RGKT    VE V KFD GCAN  NTMDYVVWTD      V Y VQD--NDT
HPV11.E2   TS YEMWLTP P         KRCFK K QGNT    VE V KFD GCED  NVMEYVVWTH      I L QD--NDS
HPV18.E2   TC EELWNTE P         THCFK K GGQT    VQ V YFD GNKD  NCMTYVAWDS      V Y Y-MTDAGT
HPV-31.E2  TS LELYLTA P         TGCLK K HGYT    VE V QFD GDVH  NTMHYTN WK F    I L CI--DGQ
HPV-1A.E2  TS RELFLAP P         AGTFK K SGST    LE V TYD NNPD  NQTRHTIWNH      V Y QN-GDDV
HPV57.E2   TC LEMWEAP P         KRCWK K KGQS    VL V KFD GSCD  RDMIYTG WG H    I V QDINDDT 154                  163                 172              182                    192
HPV16.E2   VTVVEGQ VDY          YGLY Y V-HEG     I-RTYFVQ F K   DDA EKYS KNK   VWE V HAGGQV
BPV1.E2    WQLAKAGADG           TGLY Y CTMAG     AGRIYYSR F G   DEA ARFS TTG   HYS V RDQDRV
HPV6b.E2   WVKVHSMVDA           KGIY Y T-CGQ     F-KTYYVN F V   KEA EKYG STK   HWE V CYGSTV
HPV11.E2   WVKVTSSVDA           KGIY Y T-CGQ     F-KTYYVN F N   KEA QKYG STN   HWE V CYGSTV
HPV18.E2   WDKTATCVSH           RGLY Y V-KEG     Y-NTFYIE F K   SEC EKYG NTG   TWE V HFGNNV
HPV-31.E2  CTVVEGQVNC           KGIY Y V-HEG     H-ITYFVN F T   EEA KKYG TGK   KWE V HAGGQV
HPV-1A.E2  WRKVSSGVDA           VGVY Y LEHDG     Y-KNYYVL F A   EEA SKYS TTG   QYA V NYRGKR
HPV57.E2   WHKVPGQ VDE          LGLF Y V-HDG     V-RVNYVD E G   IEA LTYG VTG   TWE V QVGGRV
```

METHODS, KITS, AND COMPOSITIONS FOR DIAGNOSING PAPILLOMAVIRUS INFECTION

FIELD OF THE INVENTION

The present invention relates to diagnosis of papillomavirus infections, and more specifically to prognostic tools for discriminating between non-cancerous, pre-cancerous, and cancerous lesions in papillomavirus infected mammals.

BACKGROUND OF THE INVENTION

Papillomaviruses are small DNA viruses of the papovavirus family that infect mammalian epithelial cells, causing epithelial proliferative lesions which may be benign, e.g., fibropapillomas (warts), or which may be malignant. All papillomaviruses are similar in that the genome size, organization, open reading frames, and protein functions are shared. Many, but not all, genome regions are conserved among the various papillomaviruses. The papillomaviruses differ, however, in host species specificity and in pathological manifestations. For example, in humans, about sixty genetically distinct strains of human papillomavirus (HPV) have been identified, many of which appear to be responsible for different disease states. "Low-risk" HPVs, e.g., HPV-6 and HPV-11, cause benign hyperplasias such as genital warts, while "high-risk" HPVs, e.g., HPV-16, HPV-18, HPV-31, HPV-33, HPV-54, and the like, can cause cancers such as cervical or penile carcinoma.

Because of the close association between the papillomavirus life cycle and the differentiation state of the host cell, the details of the papillomavirus life cycle have not been completely elucidated. It is known that papillomaviruses infect host epithelial basal cells, where the viral genomes become established and are maintained as low copy-number episomes that replicate in coordination with host cell replication. As the infected cells differentiate into keratinocytes, viral DNA is amplified and late genes are induced, and vegetative replication of the papillomavirus follows. The episomal, vegetative life cycle is characteristic of low-risk HPVs and of high-risk HPVs prior to the development of carcinomas.

In addition the vegetative, episomal life cycle described above, papillomavirus genomes can become integrated into the host cell's DNA and cause transformation, or loss of control of growth, of the infected cell. The presence of integrated HPV DNA is characteristic of most of the cancers caused by the high-risk HPVs. The high-risk HPV genome may thus be present in infected cells in episomal form, indicating a non-cancerous state, or in integrated form, indicating a cancerous or pre-cancerous state.

Replication of episomal papillomavirus genomes is initiated by coordinated binding of two viral proteins, E1 and E2, to each other and to specific genomic sequences near the viral origin of replication. When viral DNA is integrated into the genome of a host cell, the genes encoding the E1 and E2 proteins are often deleted or disrupted and thus are incapable of being expressed. The presence of the E1 or E2 proteins in an infected cell is therefore predictive that the cell contains the episomal form of the papillomavirus genome and that the cell has not progressed to a transformed or cancerous state.

The amino acid sequences of the E1 and E2 proteins of several papillomaviruses are known. SEQ ID NO:1 sets forth the amino acid sequence of the bovine papillomavirus-1 E1 protein, and SEQ ID NO:2 sets forth the amino acid sequence of the bovine papillomavirus-1 E2 protein. SEQ ID NO:3 sets forth the amino acid sequence of the HPV-16 E1 protein, and SEQ ID NO:4 sets forth the amino acid sequence of the HPV-16 E2 protein.

The regions of protein-protein interaction between the papillomavirus E1 and E2 proteins have been generally identified for bovine papillomavirus-1 (BPV-1) and for some of the HPVs. For BPV-1, a dispute exists regarding the portion of E1 required for binding to E2. Lusky et al., (1991) Proc. Natl. Acad. Sci. USA 88, 6363–6367, discloses that the carboxyl terminus of the BPV-1 E1 protein is required for interaction with the BPV-1 E2 protein. Thorner, et al. (1993) J. Virol. 67, 6000–6014, discloses that the site of interaction with BPV-1 E2 is contained within the amino-terminal 423 amino acids of BPV-1 E1. The N-terminal 162 amino acids of BPV-1 E2 have been identified as participating in the interaction of that protein with BPV-1 E1 (Yang, et al. (1991) Cold Spring Harbor Symp. Quant. Biol. LVI, 335–346).

The amino-terminal 268 amino acids of HPV-31b E1 are suggested to be sufficient to bind HPV-31b E2 in Frattini et al. (1994) Virol. 204, 799–804. Bream et al. (1993) J. Virol. 67, 2655–2663, suggests that the carboxyl terminus of HPV-11 is dispensable for complexation with HPV-11 E2, the necessary sequences occurring in in the amino-terminal 251 amino acids of HPV-11 E1. Chiang et al. (1992) J. Virol. 66, 5224–5231, suggests that the amino-terminal domain of HPV-11 E2 may interact with HPV-11 E1.

The protein-protein interaction domains of the various papillomavirus E1 and E2 proteins are believed to be similar, because E1 and E2 proteins can support replication of both homologous and heterologous papillomaviral origins (Chiang, et al. (1992) Proc. Natl. Acad. Sci. USA 89, 5799–5803).

U.S. Pat No. 5,219,990 discloses a BPV-1 E2 transactivation repressor encompassing amino acids 325 to 410 of the native BPV-1 E2 protein (SEQ ID NO:2) that functionally comprises at least the dimerization activity, but less than the DNA binding activity, of the BPV-1 E2 protein. Additional transaction repressors are disclosed which contain the entire E2 DNA binding domain but which contain mutations rendering them capable only of forming inactive heterodimers with full-length E2 and not of binding to E2 DNA binding sites.

EP 257,754 discloses peptides derived from regions of HPV-16 which are purported to be useful as broad spectrum diagnostics, vaccines, and antigenic determinants. Specifically, EP 257,754 discloses peptides derived from amino acids 75–85 of HPV-16 E2 (SEQ ID NO:4); amino acids 210–219 of HPV-16 E2 (SEQ ID NO:4); amino acids 218–230 of HPV-16 E2 (SEQ ID NO:4); amino acids 339–350 of HPV-16 E2 (SEQ ID NO:4); and amino acids 265–277 of HPV-16 E2 (SEQ ID NO:4). The diagnostics disclosed in EP 257,754 employ antibodies raised against the peptides disclosed therein.

WO 92/11290 discloses several drug screening assays which reveal binding of full-length BPV-1 E1 to full-length BPV-1 E2, both in the presence and in the absence of the BPV-1 origin of replication.

No method now exists for discerning a high-risk HPV genome in episomal form from one which is integrated into the host cell's DNA. Such a method would be a valuable tool for establishing the prognosis for development of cancer in an individual infected with a high-risk HPV.

SUMMARY OF THE INVENTION

The present inventors have for the first time isolated the functional domain of the BPV-1 E1 protein which specifically interacts with the BPV-1 E2 protein, and the functional domain of the BPV-1 E2 protein which specifically interacts with the BPV-1 E1 protein. The present inventors have also for the first time identified the functional domain of the HPV-16 E1 protein which specifically interacts with the HPV-16 E2 protein, and the functional domain of the HPV-16 E2 protein which specifically interacts with the HPV-16 E1 protein.

The identification of the functional domains of papillomavirus E1 and E2 proteins which interact with each other has allowed isolation of "papillomavirus E1/E2 interaction domains". As used herein, a papillomavirus E1/E2 interaction domain is defined as a peptide containing that portion of a papillomavirus E1 protein which interacts directly with a papillomavirus E2 protein, or as a peptide containing that portion of a papillomavirus E2 protein which interacts directly with a papillomavirus E1 protein, wherein the interaction between the E1 and E2 proteins is capable of resulting in binding to a papillomavirus origin of replication and subsequent DNA replication of a papillomavirus episome. In accordance with the present invention, papillomavirus E1/E2 interaction domain derived from a papillomavirus E1 protein is complementary to a papillomavirus E1/E2 interaction domain derived from a papillomavirus E2 protein. Similarly, a papillomavirus E1/E2 interaction domain derived from a papillomavirus E2 protein is complementary to a papillomavirus E1/E2 interaction domain derived from a papillomavirus E1 protein.

Papillomavirus E1/E2 interaction domains are used in accordance with the invention to detect the presence or absence of an episomal papillomavirus genome in a papillomavirus-infected cell. This determination forms the basis of the the claimed methods, compositions, and kits relating to diagnosis and treatment of papillomavirus infections in mammals and development of drug screening assays.

In one embodiment, the invention provides a method of determining the pathogenic status of a cell infected with papillomavirus, which comprises
 a. exposing the cell to a papillomavirus E1/E2 interaction domain for a time and at a temperature sufficient to allow binding between the papillomavirus in the cell and the E1/E2 interaction domain; and
 b. detecting the binding between the E1/E2 interaction domain and the cell, wherein a substantially non-cancerous papillomavirus-infected cell is capable of binding to the E1/E2 interaction domain, and a cancerous or pre-cancerous papillomavirus-infected cell is not capable of binding to the E1/E2 interaction domain.

The invention is also embodied as a kit for determining the pathogenic status of a papillomavirus infection which comprises:
 a) a papillomavirus E1/E2 interaction domain;
 b) a means for detecting the interaction between a papillomavirus E1 protein and a papillomavirus E2 protein.

The invention is further embodied in a method of typing human papillomavirus infections in a tissue which comprises
 a. exposing the tissue to a plurality of E1/E2 interaction domains, each E1/E2 interaction domain being characteristic of a subtype of human papillomavirus; and
 b. measuring the extent of binding between the tissue and each of the E1/E2 interaction domains, wherein the E1/E2 interaction domain having the greatest amount of binding to the tissue corresponds to the human papillomavirus subtype infecting the tissue.

In another embodiment, the invention provides a composition comprising a peptide consisting essentially of an E1/E2 interaction domain.

In another embodiment, the invention provides a method of inhibiting replication of a papillomavirus episome which comprises exposing the episome to a composition that interferes with the interaction of the episome with a papillomavirus E1 protein and a papillomavirus E2 protein.

In another embodiment, the invention provides a method of inhibiting papillomavirus infection in a cell which comprises exposing the cell to a composition that interferes with the interaction of a papillomavirus E1 protein and a papillomavirus E2 protein.

In another embodiment, the invention provides a method of inhibiting replication of a papillomavirus episome which comprises exposing the episome to a composition that inhibits transcriptional activation of the episome by a papillomavirus E2 protein.

In another embodiment, the invention provides a method of identifying an inhibitor of papillomavirus episome replication which comprises
 (a) combining a papillomaviral E1/E2 interaction domain derived from an E1 protein and a papillomaviral E1/E2 interaction domain derived from an E2 protein, to form a first binding mixture;
 (b) combining the papillomaviral E1/E2 interaction domain derived from an E1 protein, the papillomaviral E1/E2 interaction domain derived from an E2 protein, and a test compound, to form a second binding mixture; and
 (c) measuring the binding in the first and second binding mixtures,
 wherein the test compound is capable of inhibiting papillomavirus episome replication when the binding in the second binding mixture is less than the binding in the first binding mixture.

BRIEF DESCRIPTION OF THE DRAWINGS

The foregoing and other objects of the invention, the various features thereof, as well as the invention itself, may be more fully understood from the following description, when read together with the accompanying drawings in which:

FIG. 3 summarizes genetic constructs of yeast interaction trap "baits" containing various HPV-16 E1 protein and E2 protein fragments used to identify the E1/E2 interaction domains of the HPV-16 E1 and E2 proteins.

FIG. 4 is an alignment of amino acid sequences of the N-terminal region of the E2 protein of various papillomaviruses: identical amino acids are shown by white letters with black background, and related amino acids are boxed. The 24 amino acids of HPV-16 which were targeted for point mutagenesis as described in Example 2B are indicated with arrows.

DETAILED DESCRIPTION OF THE PREFERRED EMBODIMENTS

Figure 1:
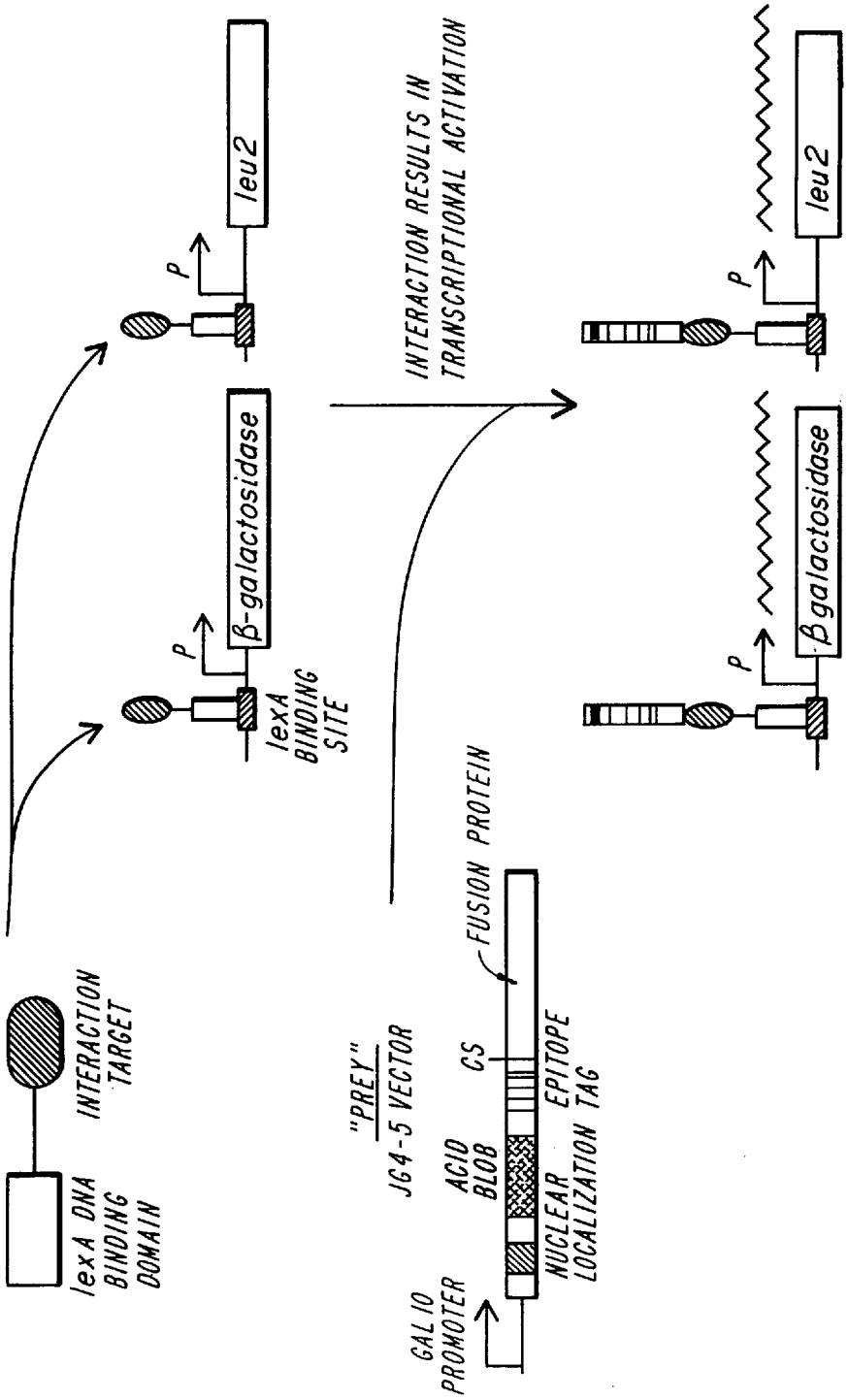
FIG. 1 depicts the prior art yeast interaction trap system (Zervos, A. S., et al. (1993) *Cell* 72, 223–232) and WO 94/10300.

The patent and scientific literature referred to herein establishes the knowledge that is available to those with skill in the art. The issued U.S. patents, allowed applications, and references cited herein are hereby incorporated by reference.

As set forth above, a papillomavirus E1/E2 interaction domain may be derived from a papillomavirus E1 protein or from a papillomavirus E2 protein. In accordance with the present invention, a papillomavirus E1/E2 interaction domain comprising a peptide derived from an E1 protein may be isolated from any papillomavirus. One such papillomavirus E1/E2 interaction domain, derived from BPV-1 E1 protein, comprises a peptide consisting essentially of amino acids 1 to 250 of SEQ ID NO:1. Another E1/E2 interaction domain derived from BPV-1 E1 protein comprises a peptide consisting essentially of amino acids 1 to 222 of SEQ ID NO:1. E1/E2 interaction domains derived from HPV-16 E1 protein include a peptide consisting essentially of amino acids 144 to 649 of SEQ ID NO:3; a peptide consisting essentially of amino acids 335 to 649 of SEQ ID NO:3; a peptide consisting essentially of amino acids 421 to 649 of SEQ ID NO:3; and the like. A papillomavirus E1/E2 interaction domain comprising a peptide derived from an E1 protein may have any amino acid sequence, so long as the peptide retains the ability to interact with a papillomavirus E2 protein.

A papillomavirus E1/E2 interaction domain comprising a peptide derived from an E2 protein may also be isolated from any papillomavirus in accordance with the present invention. A papillomavirus E1/E2 interaction domain derived from BPV-1 E2 protein comprises a peptide consisting essentially of amino acids 1 to 91 of SEQ ID NO:2. Another papillomavirus E1/E2 interaction domain, derived from HPV-16 E2 protein comprises a peptide consisting essentially of amino acids 1 to 190 of SEQ ID NO:4. A papillomavirus E1/E2 interaction domain comprising a peptide derived from an E2 protein may have any amino acid sequence, so long as the peptide retains the ability to interact with a papillomavirus E1 protein.

Figure 4:
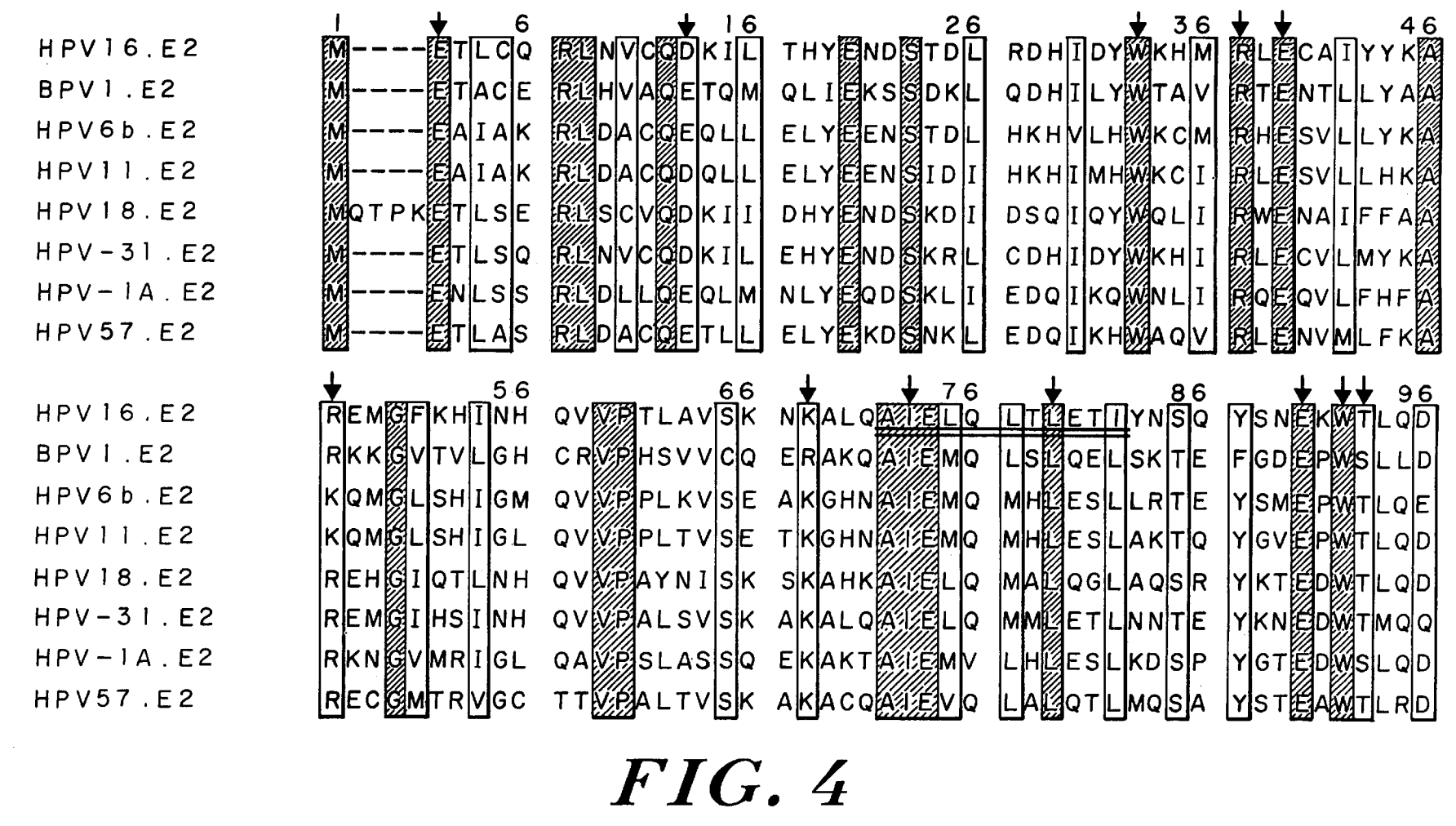

The invention also encompasses papillomavirus E1/E2 interaction domains derived from other papillomavirus E1 and E2 proteins. FIG. 4 sets forth an alignment of amino acid sequences of the N-terminal region of the E2 protein of various papillomaviruses. This alignment shows a conserved region corresponding to amino acids 1 to 141 of SEQ ID NO:2 (BPV-1 E2) and to amino acids 1 to 141 of SEQ ID NO:4 (HPV-16 E2). Because this region of the E2 protein is highly conserved among papillomaviruses, similar alignments of the N-terminal regions of other papillomavirus E2 proteins may readily be accomplished. The present inventors have discovered that glutamic acid residue 39 of SEQ ID NO:4 is absolutely required for binding of HPV-16 E2 to the HPV-16 E1 protein, as described in detail in Example 2(B)(4) below. Thus a preferred papillomavirus E1/E2 interaction domain comprising a peptide derived from an E2 protein is any papillomavirus E2-derived peptide from this conserved region that includes a glutamic acid residue at a position corresponding to amino acid residue 39 of SEQ ID NO:2 and SEQ ID NO:4 and that further retains the ability to interact with a papillomavirus E1 protein.

Additional papillomavirus E1/E2 interaction domains may be identified by substituting portions of E1 or E2 proteins derived from other papillomaviruses as "bait" in the assay depicted in FIG. 1 and described in detail in Example 1. Additional E1/E2 interaction domains may also be made by inserting, substituting, or deleting amino acids in the peptides specifically described above, using known methods. of course, such altered peptides must maintain their ability to interact with the complementary E1 or E2 interaction domain.

The peptides comprising the papillomavirus E1/E2 interaction domains of the invention may be made by any suitable method, such as by purification from papillomavirus-infected cells or by expression from transfected cells using recombinant DNA techniques. Alternatively, the papillomavirus E1/E2 interaction domain peptides may be expressed as a product of transgenic animals, e.g., as a component of the milk of transgenic cows, goats, pigs, sheep, and the like, which are characterized by somatic or germ cells containing a DNA sequence or sequences encoding the peptides.

When the papillomavirus E1/E2 interaction domain peptides used in the methods of the invention are recombinantly expressed, DNAs encoding the peptides (e.g., a DNA encoding amino acids 1 to 250 of SEQ ID NO:1; a DNA encoding amino acids 1 to 222 of SEQ ID NO:1; a DNA encoding amino acids 144 to 649 of SEQ ID NO:3; a DNA encoding amino acids 335 to 649 of SEQ ID NO:3; a DNA encoding amino acids 421 to 649 of SEQ ID NO:3; a DNA encoding amino acids 1 to 91 of SEQ ID NO:2; a DNA encoding amino acids 1 to 190 of SEQ ID NO:4) are operably linked to an expression control sequence. As defined herein, "operably linked" means enzymatically or chemically ligated to form a covalent bond between the DNA encoding the peptide and the expression control sequence, said ligation being effected in such a way that the peptide is expressed by a host cell which has been transformed (transfected) with the ligated DNA/expression control sequence. Many suitable expression control sequences are known in the art, for example, general methods of expressing recombinant proteins in mammalian cells are also known and are exemplified in R. Kaufman (1990) *Methods in Enzymology* 185, 537–566. Many DNA vectors for expression of peptides in mammalian cells are known, for example, the pcDNA3 or the pRc/RSV vectors available from Invitrogen, San Diego, Calif. U.S.A.

A number of types of mammalian cells may act as suitable host cells for expression of the papillomavirus E1/E2 interaction domain peptides of the invention. For example, suitable mammalian host cells include monkey COS cells, Chinese Hamster Ovary (CHO) cells, human C33 cells, human kidney 293 cells, human epidermal A431 cells, human Colo205 cells, mouse 3T3 cells, CV-1 cells, other transformed primate cell lines, HeLa cells, mouse L cells, baby hamster kidney (BHK) cells, HL-60 cells, U937 cells, hamster kidney (HaK) cells, or the like.

Alternatively, the papillomavirus E1/E2 interaction domain peptides of the invention may be recombinantly produced by operably linking the DNAs which encode them to suitable control sequences in one or more insect expression vectors, and employing an insect expression system. Materials and methods for baculovirus/insect cell expression systems are commercially available in kit form from, e.g., Invitrogen, San Diego, Calif. U.S.A. (the MacBac® kit) or PharMingen, San Diego, Calif. U.S.A. (the BaculoGold™ Transfection Kit). Such methods are well known in the art, as described in Summers and Smith (1987) *Texas Agricultural Experiment Station Bulletin No.* 1555, incorporated herein by reference.

The papillomavirus E1/E2 interaction domain peptides of the present invention may also be produced in lower eukaryotes such as yeast or in prokaryotes such as bacteria. When expressed in yeast, the DNAs encoding the peptides of the invention are operably linked to an expression control sequence suitable for expression in yeast. Many vectors for expression of heterologous peptides in yeast are known, for example, the pYES2 vector available from Invitrogen, San Diego, Calif. U.S.A. Potentially suitable yeast host cell strains include *Saccharomyces cerevisiae, Schizosaccharomyces pombe,* Kluyveromyces strains, Candida, or any yeast strain capable of expressing heterologous proteins. When expressed in bacteria, the DNAs encoding the papillomavirus E1/E2 interaction domain peptides of the invention are operably linked to an expression control sequence suitable for expression in bacteria. Many vectors for expression of heterologous peptides in bacteria are known. Potentially suitable bacterial host cells include *Escherichia coli, Bacillus subtilis,* attenuated strains of *Salmonella typhimurium,* and the like. When expressed in bacteria, the papillomavirus E1/E2 interaction domain peptides of the invention may be initially obtained in inclusion bodies and may be refolded using known methods and chaotropic agents. Bacterially expressed peptides in accordance with the invention may also be obtained in the form of fusion proteins, for example, as glutathione-S-transferase or β-galactosidase fusion proteins, using methods which are well known in the art, for example, using the pGEX vectors available from Pharmacia, Piscataway, N.J., U.S.A.

The papillomavirus E1/E2 interaction domains of the invention may be used to detect the presence or absence of an episomal papillomavirus genome in a papillomavirus-infected cell. This information forms the basis of the methods of the invention, which are useful for diagnosing papillomavirus diseases and for establishing prognoses of mammals infected with papillomaviruses, especially of individuals infected with human papillomaviruses.

In one embodiment, the method of the invention allows determination of the pathogenic status of a cell infected with a papillomavirus. As described above, the cancerous, pre-cancerous or non-cancerous status of a papillomavirus-infected cell correlates with the location of the viral genome within the cell and the expression level of the papillomavirus E1 or E2 proteins. In accordance with the invention therefore, a cancerous or pre-cancerous cell is defined as a cell in which the papillomaviral genome is integrated into the host genome, and in which no expression of the papillomaviral E1 or E2 proteins is detectable. Also in accordance with the invention, a substantially non-cancerous papillomavirus-infected cell is defined as a cell which contains an episomal viral genome, and in which the E1 and E2 proteins are expressed.

In accordance with the method of the invention, the pathogenic status of a cell infected with a papillomavirus is detected by exposing the cell to a papillomavirus E1/E2 interaction domain for a time and at a temperature sufficient to allow the domain to bind to any complementary papillomavirus E1 or E2 protein which may be present in the cell. Binding of the papillomavirus E1/E2 interaction domain to the cell is detected using any of a variety of suitable methods, such as by radiometric, fluorescent, or enzymatic methods. The presence of binding indicates that the papillomavirus is present in the cell as an episome and that the cell is substantially non-cancerous. The absence of binding indicates that the papilomavirus genome is integrated into the cell's genome and that the cell is pre-cancerous or cancerous. This information will allow a clinician to establish a prognosis for the infected individual.

In another embodiment, the invention allows typing of human papillomavirus infections in an infected tissue. The complete amino acid sequences of a large number of HPV subtype E1 and E2 proteins are known or can be predicted from the DNA sequences of those viruses. E1/E2 interaction domains for each of the HPV subtypes can readily be identified using the yeast interaction trap assay described in FIG. 1 and in Example 1. The HPV subtype E1/E2 interaction domains thus identified may be produced as described above.

The subtype of a HPV-infected tissue can be determined, for example, by exposing the tissue to various HPV subtype E1/E2 interaction domains, and determining the extent of binding between the tissue and the HPV subtype E1/E2 interaction domains. The HPV subtype E1/E2 interaction domain demonstrating the greatest amount of binding to the tissue corresponds to the subtype of the infecting virus.

The extent of binding between the tissue and the HPV subtype E1/E2 interaction domains may be determined by exposing the fixed tissue to one or more labeled HPV subtype E1/E2 interaction domain peptides. Preferably, the HPV subtype E1/E2 interaction domain peptides are labeled with a radioisotope such as $^3$H, $^{32}$P, $^{35}$S, $^{14}$C, $^{125}$I, and the like. More preferably, the HPV subtype E1/E2 interaction domain peptides are labeled with a fluorescent molecule such as phycoerythrin, fluorescein isocyanate, rhodamine, and the like. Most preferably, the HPV subtype E1/E2 interaction domain peptides are labeled with an enzyme such as horseradish peroxidase or alkaline phosphatase. Detection of such labeled peptides is within the level of skill in the art.

Alternatively the HPV subtype E1/E2 interaction domains may be immobilized on a solid support such as an affinity chromatographic material, or on a carrier such as in the wells of a microtiter plate. Each well or series of wells contains an E1/E2 interaction domain characteristic of a particular HPV, and appropriate controls are included. A tissue sample is prepared in such a way as to allow exposure of intracellular proteins to the immobilized HPV subtype E1/E2 interaction domains, for example, the tissue may be sonicated, homogenized, treated with detergents, and the like. Aliquots of the prepared tissue sample are added to each well of the microtiter plate, and interaction between the immobilized HPV subtype E1/E2 interaction domains in the wells is determined. Any method may be used to determine the extent of interaction between the immobilized HPV subtype E1/E2 interaction domains and the prepared tissue sample. For example, the extent of interaction may be detected using an antibody which specifically interacts with papillomavirus E1/E2 protein complexes. Interaction may be detected using radiometric, fluorescent, enzymatic, magnetic resonance methods, and the like.

The invention is also embodied as a kit for determining the pathogenic status of a papillomavirus infection using the methods described above. In this embodiment, any one or more papillomavirus E1/E2 interaction domains may be included in the kit. For example, any one or more of the following papillomavirus E1/E2 interaction domains may be included in the kit: a peptide consisting essentially of amino acids 1 to 250 of SEQ ID NO:1; a peptide consisting essentially of amino acids 1 to 222 of SEQ ID NO:1; a peptide consisting essentially of amino acids 144 to 649 of SEQ ID NO:3; a peptide consisting essentially of amino acids 335 to 649 of SEQ ID NO:3; a peptide consisting essentially of amino acids 421 to 649 of SEQ ID NO:3; a peptide consisting essentially of amino acids 1 to 91 of SEQ ID NO:2; and a peptide consisting essentially of amino acids 1 to 190 of SEQ ID NO:4. Any other papillomavirus E1/E2 interaction domain may be included in the kit, so long as it retains its ability to interact with its complementary papillomavirus E1 or E2 protein.

Any means for detecting the interaction between a papillomavirus E1 protein and a papillomavirus E2 protein may be included in the kit of the invention. For example, radioisotopic detection means such as $^3H$, $^{32}P$, $^{35}S$, $^{14}C$, $^{125}I$, and the like may be included in the kit of the invention. More preferably, a fluorescent molecule such as phycoerythrin, fluorescein isocyanate, rhodamine, and the like is included in the kit of the invention as a detection means. Most preferably, an enzyme such as horseradish peroxidase or alkaline phosphatase is included in the kit of the invention as a detection means. Alternatively other detection means, such as spin-labeled compounds, may be included in the kit of the invention.

The kit of the invention may optionally include buffers, tissue preparation reagents, tissue preparation tools, vials, and the like.

The invention as embodied in a composition comprising a peptide consisting essentially of an E1/E2 interaction domain may be used to treat papillomavirus-infected mammals. Any papillomavirus E1/E2 interaction domain may be included in the composition of the invention. For example, the composition of the invention may comprise a peptide selected from the group consisting of a peptide consisting essentially of amino acids 1 to 250 of SEQ ID NO:1, a peptide consisting essentially of amino acids 1 to 222 of SEQ ID NO:1, a peptide consisting essentially of amino acids 144 to 649 of SEQ ID NO:3, a peptide consisting essentially of amino acids 335 to 649 of SEQ ID NO:3, a peptide consisting essentially of amino acids 421 to 649 of SEQ ID NO:3, essentially of amino acids 1 to 91 of SEQ ID NO:2, and a peptide consisting essentially of amino acids 1 to 190 of SEQ ID NO:4. Alternatively, the composition of the invention may comprise any other papillomavirus E1/E2 interaction domain which retains its ability to interact with its complementary papillomavirus E1 or E2 protein.

In this embodiment, a therapeutically effective amount of the composition may be combined with a pharmaceutically acceptable carrier to treat a papillomavirus infection. In accordance with the invention, "a therapeutically effective amount" of the composition of the invention is defined as an amount sufficient to cause a decrease in papillomavirus-associated cellular proliferation. Effective amounts of the composition of the invention will vary according to factors such as the degree of susceptibility of the individual, the age, sex, and weight of the individual, and idiosyncratic responses of the individual. As used herein "pharmaceutically acceptable carrier" includes any and all solvents, dispersion media, coatings, antibacterial and antifungal agents, isotonic agents, absorption delaying agents, and the like. The use of such media and agents for pharmaceutically active substances is well known in the art. Supplementary active compounds can also be incorporated into the therapeutic compositions of the invention. The peptides of the invention may further be administered to an individual in an appropriate diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as an interferon or such as immune stimulating interleukins, for example, interleukin-4, interleukin-10, interleukin-12, and the like. Adjuvants contemplated herein include resorcinols, non-ionic surfactants such as polyoxyethylene oleyl ether and n-hexadecyl polyethylene ether. Enzyme inhibitors include pancreatic trypsin inhibitor, diethylpyrocarbonate, and trasylol. Liposomes include water-in-oil-in-water CGF emulsions as well as conventional liposomes (Strejan et al. (1984) *J. Neuroimmunol.* 7, 27).

The composition of the invention may be administered in any convenient manner such as by injection (subcutaneous, intravenous, intramuscular, intraperitoneal, or the like), oral administration, sublingual administration, inhalation, transdermal application, or rectal administration. Depending on the route of administration, composition may include a coating with a material to protect against the action of enzymes, acids and other natural conditions which may cause inactivation. Preferably, the composition of the invention is administered topically.

Replication of a papillomavirus episome may be inhibited in accordance with the invention by exposing a papillomavirus episome to a composition that interferes with the interaction of the episome with a papillomavirus E1 protein and a papillomavirus E2 protein. Similarly, papillomavirus infection in a cell may be inhibited by exposing the cell to a composition that interferes with the interaction of a papillomavirus E1 protein and a papillomavirus E2 protein. One composition capable of inhibiting replication of a papillomavirus episome and of inhibiting papillomavirus infection is the composition described above, which comprises a peptide consisting essentially of an E1/E2 interaction domain.

Other compositions capable of inhibiting replication of a papillomavirus episome and of inhibiting papillomavirus infection may be identified by screening such compositions in a screening assay which detects a change in the interaction between a papillomaviral E1/E2 interaction domain derived from an E1 protein and a papillomaviral E1/E2 interaction domain derived from an E2 protein. Any papillomaviral E1/E2 interaction domain may be used to screen for compounds capable of inhibiting the interaction between the papillomaviral E1 and E2 proteins. For example, a papillomaviral E1/E2 interaction domain derived from an E1 protein may comprise a peptide selected from the group consisting of a peptide consisting essentially of amino acids 1 to 250 of SEQ ID NO:1, a peptide consisting essentially of amino acids 1 to 222 of SEQ ID NO:1, a peptide consisting essentially of amino acids 144 to 649 of SEQ ID NO:3, a peptide consisting essentially of amino acids 335 to 649 of SEQ ID NO:3, and a peptide consisting essentially of amino acids 421 to 649 of SEQ ID NO:3 and any of these peptides may be used to screen for inhibitors. A papillomaviral E1/E2 interaction domain derived from an E2 protein may comprise a peptide selected from the group consisting of a peptide consisting essentially of amino acids 1 to 91 of SEQ ID NO:2 and a peptide consisting essentially of amino acids 1 to 190 of SEQ ID NO:4, and either of these peptides may be used to screen for inhibitors of papillomaviral episome replication and papillomaviral infection.

Any assay may be used to screen for compounds capable of inhibiting replication of a papillomavirus episome and of inhibiting papillomavirus infection in accordance with the present invention. For example, a papillomavirus E1/E2 interaction domain may be fused to the DNA binding domain of a sequence-specific DNA binding protein such as lex A (described in example 1A), and a complementary papillomavirus E1/E2 interaction domain may be fused to a second protein containing a suitable transcriptional activation domain. Interaction between the two fusion proteins is detected by transcriptional activation of a reporter gene, as described in detail in WO 94/10300 and in Example 1A below. Test compounds capable of inhibiting the interaction between the complementary papillomavirus E1/E2 interactions domains are capable of inhibiting replication of a papillomaviral episome or of inhibiting papillomaviral infection.

Binding assays using a desired binding protein are well known in the art and may be used to screen for compounds capable of inhibiting the interaction between a papillomaviral E1 protein and a papillomaviral E2 protein. The papillomaviral E1/E2 interaction domains identified above may be used in such binding assays. The papillomaviral E1/E2 interaction domains of the invention may optionally be fused to another protein such as glutathione-S-transferase (GST), E. coli maltose binding protein (MBP), epitope tags, and the like, and used in a binding assay to screen for compounds capable of inhibiting the interaction between the papillomaviral E1 and E2 proteins.

In order to identify compositions which act by interfering with the interaction between a papillomaviral E1 protein and a papillomaviral E2 protein, a first binding mixture is formed by combining a papillomaviral E1/E2 interaction domain derived from an E1 protein and a papillomaviral E1/E2 interaction domain derived from an E2 protein, and the amount of binding in the first binding mixture ($B_0$) is measured. A second binding mixture is formed by combining a papillomaviral E1/E2 interaction domain derived from an E1 protein, a papillomaviral E1/E2 interaction domain derived from an E2 protein, and the test compound or agent to be screened, and the amount of binding in the second binding mixture (B) is measured. The amounts of binding in the first and second binding mixtures are compared, for example, by performing a $B/B_0$ calculation. A compound or agent is considered to be capable of inhibiting replication of a papillomaviral episome or of inhibiting papillomaviral infection if a decrease in binding in the second binding mixture as compared to the first binding mixture is observed.

In performing the binding assay, a papillomaviral E1/E2 interaction domain derived from an E1 protein may optionally be immobilized on a carrier and binding to a soluble papillomaviral E1/E2 interaction domain derived from an E2 protein may be measured in the presence and in the absence of potential inhibiting agents. Alternatively, a papillomaviral E1/E2 interaction domain derived from an E2 protein may be immobilized on a carrier and binding to a soluble papillomaviral E1/E2 interaction domain derived from an E1 protein may be measured in the presence and in the absence of potential inhibiting agents.

In vitro binding interactions between E1/E2 interaction domains are affected by the temperature at which such binding reactions are carried out. As described in Example 1(D) below, the BPV-1 E1/E2 interaction was significantly decreased at 4° C. as compared to 22° C. (room temperature). Such temperature-mediated effects are indicative of conformational changes in one or both of the interacting molecules. For this reason, the binding assays described above may optionally be performed at various temperatures, to address the possibility that some candidate test compounds may have a different effect on the E1/E2 interaction at different temperatures. Test compounds exhibiting such behavior may actively alter the conformation of E1 or E2 by forcing the protein into a state in which an E1/E2 complex does not occur. Alternatively, such compounds might prevent disassociation of an E1/E2 complex formed at the permissive temperature (22° C.) when shifted to the non-permissive temperature (4° C.).

The formulation and optimization of binding mixtures is within the level of skill in the art. Such binding mixtures may optionally contain buffers and salts necessary to enhance or to optimize binding, and additional control assays may be included in the screening assay of the invention. Compounds found to reduce by at least about 10%, preferably greater than about 50% or more of the binding between a papillomaviral E1/E2 interaction domain derived from an E1 protein and a papillomaviral E1/E2 interaction domain derived from an E2 protein may thus be identified and then secondarily screened in other assays, including assays of binding to interaction domains derived from different papillomavirus subtypes. Additional secondary screens may be based on the transient replication assay of Example 2(B) (3) below. By these means compounds having inhibitory activity for papillomaviral episome replication and for papillomaviral infection which may be suitable as anti-papillomavirus agents may be identified.

Inhibition of papillomavirus episome replication and papillomavirus infection may also occur in accordance with the present invention through inhibition of the transcriptional activation function of a papillomaviral E2 protein in an infected cell. One composition capable of inhibiting transcriptional activation is a peptide consisting essentially of amino acids 53 to 161 of SEQ ID NO:2. The conserved region of papillomavirus E2 proteins described above, corresponding to amino acids 1 to 141 of SEQ ID NO:2 (BPV-1 E2) and to amino acids 1 to 141 of SEQ ID NO:4 (HPV-16 E2) is depicted in FIG. 4. The present inventors have discovered that isoleucine residue 73 is absolutely required for the transcriptional activation function of HPV-16 E2, as described in detail in Example 2(B) (4) below. Thus a preferred peptide derived from an E2 protein capable of inhibiting transcriptional activation is any papillomavirus E2-derived peptide from this conserved region that includes an isoleucine residue at a position corresponding to amino acid residue 73 of SEQ ID NO:2 and SEQ ID NO:4 and that further retains the ability to bind to E2 recognition sites on a papillomavirus episome. The transcriptional activation assay of WO 94/10300 and Example 1A may be modified to screen for compositions capable of interfering with the transcriptional activation function of a papillomaviral E2 protein in a cell. In such an assay, a peptide consisting essentially of amino acids 53 to 161 of SEQ ID NO:2 is fused to a DNA binding protein such as lexA. As set forth in Example 1B, this fusion protein exhibits significant transcriptional activation in the absence of a complementary "prey" protein. Test compounds may therefore be screened for their ability to cause a decrease in transcriptional activation mediated by the fusion protein containing amino acids 53 to 161 of SEQ ID NO:2.

The following examples illustrate the preferred modes of making and practicing the present invention, but are not meant to limit the scope of the invention since alternative methods may be used to obtain similar results.

EXAMPLE 1

IDENTIFICATION OF BPV-1 E1/E2 PROTEIN INTERACTION DOMAINS

A. THE YEAST INTERACTION TRAP SYSTEM

The system employed to identify the BPV-1 E1/E2 interaction domains is the Yeast Interaction Trap System of Zervos, A. S. et al. (1993) Cell 72, 223–232 (also described in WO 94/10300). In this system, two fusion proteins are co-expressed in yeast which contain a reporter vector. One of the fusion proteins, called the "bait", comprises a first protein or protein domain fused to the DNA binding domain of the sequence-specific DNA binding protein lexA.

The bait fusion protein binds as a dimer to operator sequences positioned within the promoters of two genes on the reporter vector: the leu2 auxotrophic marker integrated into the yeast genome; and the β-galactosidase gene. The second fusion protein, called the "prey," comprises a second protein which specifically interacts with the first protein fused to an acidic activation domain that serves as an extremely potent transcriptional activator in yeast. If the bait and prey fusion proteins interact, the reporter genes on the reporter vector will be transcriptionally activated, resulting in β-galactosidase activity and leucine auxotrophy.

The lexA operator reporter vector used to identify the BPV-1 E1 and E2 interaction domains, JK103, (Kamens et al. (1991) *New Biologist* 3:1005–1013), contains two high affinity ColE1 lexA operators upstream of the GAL1-lacZ gene. This vector expresses the yeast URA3 selectable marker, along with the 2 μm origin of replication. LEU2, the auxotrophic marker reporter gene in this system, is integrated into the EGY048 host chromosome and contains six upstream lexA operator sites.

The bait fusion proteins used to identify the BPV-1 E1 and E2 interaction domains were expressed from the plex202 vector (Brent et al. (1985) *Cell* 43:729–736). The pLex202 vector contains the first 202 amino acids of the lexA protein, as well as the yeast HIS3 gene as a selectable marker and the 2μ origin of replication. Expression of lexA fusion proteins from this vector is driven by the constitutively active yeast ADH1 promoter.

The prey fusion proteins used to identify the BPV-1 E1 and E2 interaction domains were expressed from the pJG4-5 vector, construction of which is described in WO 94/10300. Fusion proteins expressed from this vector contain several features including a nuclear localization signal, a hemagglutinin epitope tag, and the acidic activation domain referenced above. Expression of fusion proteins from the pJG4-5 vector is under control of the yeast GAL-1 promoter, rendering their expression galactose inducible and glucose repressible.

B. BPV-1 E1/E2 INTERACTION DOMAINS

Figure 2:
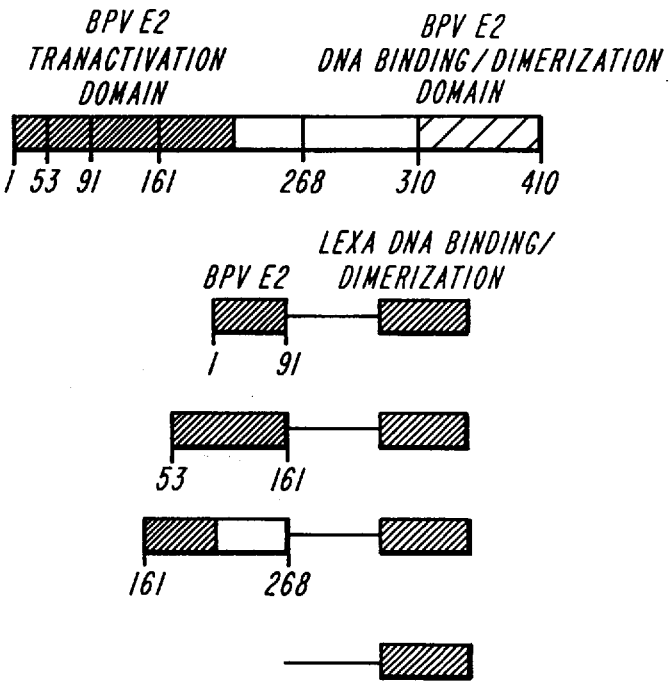
FIG. 2 summarizes genetic constructs of yeast interaction trap "baits" containing various BPV-1 E1 protein and E2 protein fragments used to identify the E1/E2 interaction domains of the BPV-1 E1 and E2 proteins.
Figure 2:
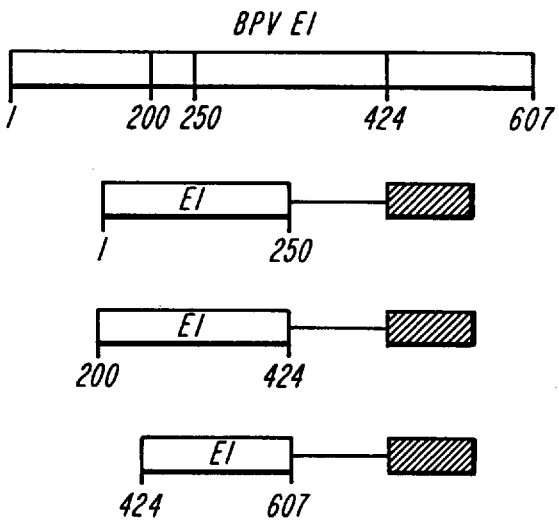

FIG. 2 indicates portions of the BPV-1 E1 and E2 proteins that were tested in yeast interaction trap system. DNAs encoding the indicated E2 fragments were generated by polymerase chain reaction using appropriate synthetic oligonucleotides, and cloned as EcoRI-SalI restriction fragments into the pLex202 vector for expression as bait fusion proteins to the lexa DNA binding domain. The indicated portions of the BPV-1 E1 open reading frame were cloned into the JG4-5 vector as EcoRI-XhoI fragments following polymerase chain reaction using appropriate synthetic oligonucleotides.

The bait and prey vectors, along with the JK103 reporter vector, were introduced into W3031A or EGY048 by a modification of the lithium acetate technique (Gietz et al. (1992) *Nucleic. Acids. Res.* 20:1425). Yeast strain W3031 (ura3, his3, trp1, ade1, leu2) was the gift of R. Rothstein, Columbia University, New York, N.Y., U.S.A., and yeast strain EGY048 (MATa, ura3, his3, trp1, LEU2::pLexAop6-LEU2) is described in WO 94/10300.

Yeast cultures were maintained in SD minimal medium (Sherman et al., *Methods in Yeast Genetics* (Cold Spring Harbor Laboratory Press, 1986) containing the appropriate amino acid supplements, except under induction conditions, when SG minimal medium (Sherman, et al., supra) was used. Leucine auxotrophy was determined by assessing growth on parallel minimal SD and SG plates in which leucine was included or omitted.

For the two hybrid approach to work, the bait fusion protein must have no intrinsic transcriptional activation capacity. A BPV-1 E2/lexA fusion protein containing E2 amino acids 53–161 of SEQ ID NO:2, a central portion of the BPV-1 E2 transcription activation domain, exhibited significant transcriptional properties in this context, making it unsuitable for use as bait in the yeast interaction trap system. None of the segments of the BPV-1 E1 protein tested exhibited any transcriptional activation activity.

LexA fusion proteins containing portions of the BPV-1 E2 protein (amino acids 1–91 of SEQ ID NO:2 and amino acids 161–262 of SEQ ID NO:2) were used as bait to detect interaction with portions of the BPV-1 E1 protein in yeast strain EGY 048. A lexA fusion bait containing amino acids 200–424 of the BPV-1 E1 protein (amino acids 200–424 of SEQ ID NO:1) was used as a negative control. Several segments of the BPV-1 E1 protein (amino acids 1 to 250 of SEQ ID NO:1; amino acids 200 to 424 of SEQ ID NO:1; and amino acids 424 to 605 of SEQ ID NO:1) were expressed as prey from the JG4-5 vector.

Amino acids 1–250 of the BPV-1 E1 protein scored for interaction with the lexA fusion protein containing amino acids 1–91 of BPV-1 E2, but not with a lexA fusion containing amino acids 161–262 of BPV-1 E2. This activation phenotype was dependent upon growth in galactose medium. No other portion of BPV-1 E1 protein scored for interaction. Galactose-induced expression of BPV-1 E1 fusion proteins from the JG4-5 vector was confirmed by Western blot analysis using a monoclonal antibody specific for the acidic transcriptional activation domain of E1.

These results show that the E1/E2 interaction domain derived from the BPV-1 E1 protein comprises a peptide consisting essentially of amino acid 1 to amino acid 250 of SEQ ID NO:1, and that the E1/E2 interaction domain derived from the BPV-1 E2 protein comprises a peptide consisting essentially of amino acid 1 to amino acid 91 of SEQ ID NO:2.

C. DETECTION OF BPV E1/E2 COMPLEXES in vitro

To confirm and extend the results described in experiments using the yeast interaction trap system, DNA encoding domains of the BPV-1 E1 protein were cloned into the pGEX4T-1 vector for expression as glutathione-S-transferase (GST) fusion proteins in *E. coli*. These proteins were purified by binding to glutathione beads, and their abilities to bind in vitro-translated, radiolabelled BPV-1 E2 protein were determined.

Fragments of BPV-1 E1 DNA were generated by the polymerase chain reaction using appropriate oligonucleotide primers and cloned as EcoRI-SalI fragments into the EcoRI-XhoI sites of the pGEX 4T-1 vector (Pharamacia, Madison, Wis.). Glutathione-S-transferase (GST) fusion proteins were induced and harvested as described by Kaelin et al. (*Cell* (1992) 70:351–364. Approximately 0.5 μg of each GST-E1 fusion protein was used in each binding reaction. In GST-E1 binding experiments, $^{35}$S-methionine-labelled E2 was generated using the T7-TNT coupled retiuclocyte lysate system (Promega, Madison, Wis.). Full length E2 was generated using the plasmid pCMV E2 (gift of Jean-Michelle Gauthier, Pasteur Institute, Paris, FR) as a template. Linear E2 templates encoding open reading frames for the amino terminal 262, 161, and 91 amino acids were generated by PCR using a 5' oligonucleotide that contained a T7 promoter and an initiation methionine codon in optimal Kozak context (M. Kozak (1987) *Nucleic Acids Res.* 15, 8125–8149. Templates encoding E2 (aa161–410) and E2 (Δ159–281) were generated by linearization of plasmids p2423, and p2439, respectively (McBride et al. (1988) *EMBO J.* 7:533–539).

Unless otherwise indicated, GST-E1 fusion proteins bound to glutathione Sepharose beads (Pharmacia, Madison, Wis., U.S.A.) were preincubated with agitation for 30 minutes at room temperature in 0.5 ml binding buffer [20 mM Tris, pH 7.5, 100 mM NaCl, 2 mM DTT, 5 mM MgCl₂, 0.5% NP-40 with 2% nonfat dry milk. Ten μl aliquots of 50 μl in vitro translation reactions containing radiolabelled BPV-1 E2 or RPA3 protein were then added, and incubation was continued at room temperature for 30 minutes. After three 0.5 ml washes in binding buffer without milk, samples were analyzed by 12% SDS-PAGE electrophoresis.

Radiolabelled bands were visualized by autoradiography and quantitated by phosphor image analysis using a GS-250 Molecular Image Analyzer (Biorad, Hercules, Calif., U.S.A.). In temperature sensitivity experiments, preincubation, binding reactions, and washes were carried out at the temperatures indicated. Bound proteins were detected by autoradiography, and quantitated by phosphorimager analysis (Biorad, Hercules, Calif., U.S.A.).

GST fusion proteins containing either the first 220 or 250 amino acids of the BPV-1 E1 protein (amino acid 1 to amino acid 220 of SEQ ID NO:1 and amino acid 1 to amino acid 220 of SEQ ID NO:1) bind radiolabeled BPV-1 E2 protein. In contrast, the GST fusion proteins containing amino acids 1–128, 200–424, or 424–607 of SEQ ID NO:1 had only background binding to E2. A GST fusion protein containing BPV-1 E1 amino acids 1–128 did not bind BPV-1 E2 protein in vitro, indicating that a peptide consisting essentially of amino acid 1 to amino acid 128 of the BPV-1 E1 protein is not sufficient for E2 association.

BPV-1 E1-GST fusion proteins were also used to confirm the location of E1 interaction domains within the BPV-1 E2 protein. A BPV-1 E1-GST fusion protein containing amino acids 1–222 was tested for binding to various deleted and truncated forms of BPV-1 E2 expressed as $^{35}$S-methionine-labelled proteins in reticulocyte lysates. BPV-1 E1 (amino acids 1–222)-GST fusion proteins bound to truncated forms of the BPV-1 E2 protein that encompassed the first 262, 161, or 91 amino acids of E2, confirming that the amino terminal 91 amino acid domain of the BPV-1 E2 protein is sufficient for E1 interaction. In contrast, BPV-1 E1 (amino acids 1–222)-GST did not bind to BPV-1 E2 proteins bearing deletions of the amino terminal 52 or 161 amino acids. Deletion of the hinge region of BPV-1 E2 (amino acids 159–281) did not abolish its ability to bind E1 (amino acids 1–222)-GST. Indeed, binding of the hinge-deleted E2 protein appeared to be significantly higher than that of full length E2. E1 (amino acids 1–222)-GST bound to shorter forms of BPV-1 E2 such as the E2TR and a form of E2 that is initiated at the amino acid 71 methionine residue of BPV-1 E2. BPV-1 E1 binding to all three truncated E2 species was appreciable, with all three represented in approximately the same relative amounts.

In summary, the data from these in vitro binding experiments confirm that the E1/E2 interaction domain of BPV-1 E2 comprises a peptide consisting essentially of amino acid 1 to amino acid 91 of SEQ ID NO:2.

D. COLD SENSITIVITY OF BPV-1 E1/E2 INTERACTION

The in vitro interaction of BPV-1 E1 and E2 is cold sensitive. Binding reactions of BPV-1 E1-GST (1–222) to $^{35}$S methionine-labelled full length BPV-1 E2 were performed as set forth above, except preincubation, binding reactions, and washes were performed at room temperature (about 22° C.) or at 4° C. BPV-1 E2 bands were visualized by autoradiography and quantitated by phosphor image analysis. The results demonstrated that E1/E2 interaction was significantly decreased at 4° C., relative to the level of interaction observed at room temperature.

EXAMPLE 2

IDENTIFICATION OF HUMAN PAPILLOMAVIRUS-16 E1/E2 PROTEIN INTERACTION DOMAINS

A. HUMAN PAPILLOMAVIRUS-16 E1/E2 INTERACTION DOMAINS

FIG. 3 indicates portions of the HPV-16 E1 and E2 proteins that were tested in yeast interaction trap system described in Example 1A above. DNAs encoding the indicated HPV-16 E1 fragments were generated by polymerase chain reaction using appropriate synthetic oligonucleotides, and cloned as EcoRI-SalI restriction fragments into the pLex202 vector for expression as bait fusion proteins to the lexA DNA binding domain. The indicated portions of the HPV-16 E2 open reading frame were cloned into the JG4-5 vector as EcoRI-XhoI fragments following polymerase chain reaction using appropriate synthetic oligonucleotides.

The bait and prey vectors were introduced into yeast strain EGY048, along with the JK103 reporter vector, as set forth above. Yeast cultures were maintained as set forth above. Leucine auxotrophy was determined by assessing growth on parallel minimal SD and SG plates in which leucine was included or omitted.

HPV-16 E1/lexA fusion proteins which exhibited significant transcriptional properties (amino acids 1–149 of SEQ ID NO:3; amino acids a-190 of SEQ ID NO:3; amino acids 1–437 of SEQ ID NO:3; amino acids 144–376 of SEQ ID NO:3) were not used as bait in the yeast interaction trap system. LexA fusion proteins containing full length HPV-16 E1 (amino acids 1 to 649 of SEQ ID NO:3) and the remaining portions of the HPV-16 E1 protein indicated in FIG. 3 (amino acids 1 to 272 of SEQ ID NO:3; amino acids 1 to 337 of SEQ ID NO:3; amino acids 144 to 337 of SEQ ID NO:3; amino acids 144 to 437 of SEQ ID NO:3; amino acids 144 to 482 of SEQ ID NO:3; amino acids 144 to 577 of SEQ ID NO:3; amino acids 144 to 649 of SEQ ID NO:3; amino acids 217 to 649 of SEQ ID NO:3; amino acids 335 to 649 of SEQ ID NO:3; amino acids 421 to 649 of SEQ ID NO:3; amino acids 478 to 649 of SEQ ID NO:3; amino acids 144 to 649:Δ338–420 of SEQ ID NO:3; amino acids 144 to 649:Δ438–496 of SEQ ID NO:3; and amino acids 144 to 649:Δ438–545 of SEQ ID NO:3) were used as bait to detect interaction with full-length HPV-16 E2 protein in yeast strain EGY 048. The JG4-5 vector was used as a negative control.

Full-length HPV-16 E2 (amino acids 1 to 365 of SEQ ID NO:4) and several portions of the HPV-16 E2 protein (amino acids 1 to 106 of SEQ ID NO:4; amino acids 61 to 190 of SEQ ID NO:4; amino acids 164 to 245 of SEQ ID NO:4; amino acids 1 to 150 of SEQ ID NO:4; amino acids 33 to 190 of SEQ ID NO:4; amino acids 1 to 190 of SEQ ID NO:4; amino acids 61 to 245 of SEQ ID NO:4; amino acids 1 to 245 of SEQ ID NO:4; and amino acids 164 to 365 of SEQ ID NO:4) were expressed as prey from the JG4-5 vector, using either full-length HPV-16 E1 or HPV-16 E1 (amino acids 144 to 649) as bait.

Amino acids 144 to 649, 335 to 649, and 421 to 649 of the HPV-16 E1 protein scored for interaction with full-length HPV-16 E2 protein. Amino acids 1 to 190 of the HPV-16 E2 protein interacted with either full-length HPV-16 E1 protein or with HPV-16 E1 (amino acids 144 to 649).

These results show that the E1/E2 interaction domain derived from the HPV-16 E1 protein comprises a peptide selected from the group consisting of a peptide consisting essentially of amino acid 144 to amino acid 649 of SEQ ID NO:3, a peptide consisting essentially of amino acid 335 to amino acid 649 of SEQ ID NO:3, and a peptide consisting essentially of amino acid 421 to amino acid 649 of SEQ ID NO:3. The E1/E2 interaction domain derived from the HPV-16 E2 protein comprises a peptide consisting essentially of amino acid 1 to amino acid 190 of SEQ ID NO:4.

B. MUTAGENESIS STUDIES OF THE E1/E2 INTERACTION DOMAIN DERIVED FROM HPV-16 E2 PROTEIN

1. Generation of mutants

Amino acids important in the interaction of the HPV-16 E1/E2 interaction domain derived from the HPV-16 E2 protein were identified using structure-function studies of a series of 24 point mutants in the E2 N-terminal region. The point mutations generated resulted in alanine substitutions at the sites indicated by arrows in FIG. 4.

All point mutations were introduced into the HPV-16 E2 sequence by the polymerase chain reaction directed mutagenesis method (Cormack, in *Current Protocols in Molecular Biology*, Asubel, F. M. et al., eds., John Wiley and Sons (New York, 1987) with the primers designed to change each target codon to ACG. The DNA fragments produced from the polymerase chain reaction were cloned into pUC vectors and their sequences were confirmed by sequencing. Plasmid pCMV-E2$_{16}$ has been described (Del Vecchio, et al. (1992), *J. Virol.* 66, 5949–5958), which contains the HPV-16 DNA fragment excised from pSK-E2$_{16}$ (nt 2756 to 3855) cloned into the BglI-SmaI sites of the cytomegalovirus (CMV) immediate-early promoter/enhancer-base expression vector pCMV4.

The E2 mutants were designated with the targeted amino acid (single letter) and its position (first methionine of E2 open reading frame=1). For example, the mutant containing a point mutation in tryptophan 33 was designated as W33. The mutant HPV-16 E2-expression vectors were constructed by exchanging a DNA fragment containing the desired mutation with the corresponding DNA fragment on the wild type HPV-16 E2 gene using available restriction sites. For example, the W33 mutant was constructed by insertion of a stop codon linker (NheI linker #1060, New England Biolabs) into the gall site at nt 3401 in the HPV-16 E2 DNA sequence of pCMV-E2$_{16}$.

2. Transcriptional Activation Assay

The HPV-1 E2 mutants were analyzed for transcriptional activator function using the chloramphenicol acetyltransferase (CAT) assay of Gorman, et al. (1982) *Mol. Cell. Biol.* 2, 1044–1051. Two CAT-expressing reporter constructs were used to determine transactivator function: the p6xE2BStkCAT plasmid contains the thymidine kinase (tk) promoter of herpes simplex virus and six tandem repeats of the E2 binding motif characteristic of the papillomavirus genome, and p16E contains the SV40 early promoter and the HPV-16 LCR which contains three such E2 binding motifs.

Five µg of each mutant HPV-16 E2-expression vector was co-transfected with 1 µg of a reporter plasmid into CV1 cells (CCL 70) or into C33A cells (ATCC accession # HTB3 1), and 1 µg pSVβ (Clonetech Laboratories, Inc.) control plasmid, using the calcium phosphate precipitation method as described in Kingstone, *Current Protocols in Molecular Biology*, Ausubel, F. M. et al., eds., John Wiley and Sons (New York, 1987). The total amount of DNA in each transfection was adjusted to 13 µg with herring sperm DNA. Two days after transfection, cell extracts were prepared by freeze-thawing in 0.25M Tris.HCl pH 8.0, and the CAT activity of equal aliquots of the transfected cells was determined. For evaluation of the data of CAT assay, the results were normalized with transfection efficiency estimated by β-galactosidase activity which was expressed in transfected cells from the pSVβ plasmid. The results of the transactivation experiments with each mutant form of HPV-16 E2 are summarized in Table 1.

3. Transient Replication Assay

The HPV-16 E2 mutants were assayed for their ability to mediate transient replication of the HPV-16 ori-containing plasmid p16ori described in Del Vecchio, et al. (1992) *J. Virol.* 66, 5949–5958. The pCMV-E1$_{16}$ plasmid used for these experiments was constructed by inserting a HPV16 DNA fragment (nt 865-2813) to which the Kozac consensus sequence and convenient restriction enzyme sites had been added, into the BglII-SmaI sites of pCMV4.

C33A cells were co-transfected by calcium phosphate precipitation or electroporation with 1 µg p16ori and/or 5 µg pCMV-E1$_{16}$ and/or 5 µg pCMV-E2$_{16}$ expressing wild type or mutant forms of HPV-16 E2. Seventy hours after transfection, low molecular-weight DNA was extracted by the method of Hirt (B. Hirt (1967) *J. Mol. Biol.* 26, 365–369) as modified below. Plates were washed two times with phosphate-buffered saline without magnesium or calcium (PBS). The cells were then scraped into a 1.5 ml tube, pelleted, resuspended in 200 µl of buffer I (50 mM glucose, 25 mM Tris.HCl pH 8.0, 10 mM EDTA, 100 mg/ml RNase A), and lysed by the addition of 200 µl of buffer II (1% sodium dodecyl sulfate, 0.2N NaOH). After 5 min, 200 µl of ice-cold buffer III (3M–5M potassium acetate) was added and the samples were placed at 4° C. for more than 1 hour. After being centrifuged for 10 min. at 4° C., DNA was extracted once with buffer-saturated phenol, once with phenol-chloroformisoamyl alcohol, and precipitated with ethanol.

To distinguish replicated DNA from input DNA, the extracted DNA samples were digested with DpnI. Plasmid DNA had been prepared by a dam-methylase positive strain, so it was sensitive to DpnI digestion. To linearize pl6ori, the sample DNAs were digested also with XmnI. The digested samples were separated by 1.0% agarose gel electrophoresis and then analyzed by Southern blotting, using a $^{32}$P-labeled probe generated with a random-primed labeling kit (Stratagene) to label the pl6ori-specific DNA fragment containing the lacZ-coding and HPV-16 ori sequences, which was produced by polymerase chain reaction amplification. Alkaline transfer to Hybond-N+membranes (Amersham) was performed following the manufacturer's method. Hybridization in 50% formamide-containing buffer (0.5× SSC) at 42° C., with sequential washes of 0.5×SSC and 0.1×SSC at 42° C.

The sample DNA digested with DpnI and XmnI was also subjected to polymerase chain reaction-Southern blot analysis. To amplify DpnI digestion-resistant (replicated) DNA, primers (1814–1843, 2628–2657 of pKS(-)bluescriptII, Stratagene; GenBank X52327) were used with 10 cycles of polymerase chain reaction amplification. The amplified DNA was analyzed as described above. A Phosphorimager (Bio-Rad) was used for the quantitation of the hybridized signals. The amount of the template DNA for amplification was confirmed to be within the quantitative range (input DNA=0.1~50 pg).

The results of the transient replication experiments with each mutant form of HPV-16 E2 are summarized in Table 1.

4. HPV-16 E1-E2 in Vitro Interaction

The HPV-16 E2 mutant proteins were assayed for their ability to bind to HPV-16 E1 protein in an in vitro translation system.

The templates for in vitro translation were prepared by introducing the T7 promoter sequence on the 5' end of each template DNA using a T7 promoter-containing primer for PCR amplification. In vitro translations were performed with TNT-reticulocyte lysate in vitro translation reagents (ProMega Corp.) following the manufacturer's protocol. E1 protein was translated with $^{35}$S methionine and E2 proteins were translated with non-radiolabeled methionine. In vitro E1-E2 binding experiments were performed with immunoprecipitation with an anti E2(C) antiserum which had been prepared by immunizing rabbits with a purified glutathione- S-transferase-E2C protein which contained the carboxyl terminal residues 194 to 365 of the HPV-16 E2 protein (SEQ ID NO:4).

15 μl of the E1 translation reaction mixture and 5 μl of E2 translation reaction mixture were incubated in 500 μl of NET-gel buffer (50 mM Tris.HCl pH 7.5, 150 mM NaCl, 0.1% NP-40, 1 mM EDTA pH 8.0, 0.25% gelatin, 0.02% NaN$_3$) at 4° C. for one hour. Two ml of the anti E2(C) antiserum was then added, and the mixture was incubated at 4° C. for one hour followed by precipitation of the immune complexes by protein A-Sepharose beads (Pharmacia). Precipitated proteins were lysed in sodium dodecyl sulfate-polyacrylamide gel electrophoresis sample buffer and analyzed with sodium dodecyl sulfate-polyacrylamide gel electrophoresis and autoradiography.

The results of the in vitro E1-E2 interaction experiments with each mutant form of HPV-16 E2 are summarized in Table 1. One mutant, designated E39, was unable to bind to HPV-16 E1 in addition to losing the ability to function as a replication factor, indicating that the glutamate residue at position 39 of HPV-16 E2 is involved in the E1/E2 protein-protein interaction.

In Table 1 activities are indicated as follows: +++: >80% of wild type activity; ++: 40 to 80% of wild type activity; +: 5–40% of wild type activity; −: <5% of wild type activity.

TABLE 1

| E2 PROTEIN | TRANSACTIVATOR | DNA REPLICATION | E1–E2 BINDING |
| --- | --- | --- | --- |
| wild type | +++ | +++ | +++ |
| E2* | + | + | +++ |

TABLE 1-continued

| E2 PROTEIN | TRANSACTIVATOR | DNA REPLICATION | E1–E2 BINDING |
| --- | --- | --- | --- |
| D13 | +++ | ++ | ++ |
| W33 | + | + | + |
| R37 | − | + | +++ |
| E39 | +++ | − | − |
| R47 | +++ | ++ | +++ |
| K68 | ++ | ++ | +++ |
| I73 | − | +++ | +++ |
| L79 | +++ | +++ | ++ |
| E90 | +++ | +++ | +++ |
| W92 | − | + | + |
| T93 | +++ | ++ | +++ |
| E100 | +++ | ++ | +++ |
| K112 | + | ++ | ++ |
| E118 | +++ | ++ | ++ |
| F121 | +++ | + | + |
| D122 | +++ | ++ | + |
| W134* | − | + | + |
| Y138 | ++ | + | ++ |
| Y158 | +++ | ++ | +++ |
| Y167 | +++ | +++ | ++ |
| D174 | +++ | +++ | +++ |
| K177 | +++ | +++ | ++ |
| Y178 | +++ | ++ | + |

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A peptide consisting of the amino acid sequence selected from the group consisting of (a) amino acids 144 to 649 of SEQ ID NO: 3, (b) amino acids 335 to 649 of SEQ ID NO: 3, (c) amino acids 421 to 649 of SEQ ID NO: 3, and (d) amino adds 1 to 190 of SEQ ID NO: 4, wherein said peptide is a human papilloma virus 16 (HPV-16) E1/E2 interaction domain.

2. An in vitro method of inhibiting replication of a human papillomavirus 16 (HPV-16) episome which comprises exposing the episome to the peptide of claim 1 that interferes with the interaction of the episome with a papillomavirus E1 protein and a papillomavirus E2 protein.

3. An in vitro method of identifying a potential inhibitor of human papillomavirus 16 (HPV-16) episome replication which comprises:

(a) combining a peptide selected from the group consisting of peptides a, b and c of claim 1 obtained from an E1 protein and peptide d of claim 10 derived from an E2 protein, to form a first binding mixture;

(b) combining a peptide selected from the group consisting of peptides a, b, and c of claim 1 obtained from an E1 protein, peptide d of claim 1 derived from an E2 protein, and a test compound, to form a separate second binding mixture;

(c) measuring the binding in the first and second binding mixtures, and (d) comparing the measured binding between the first and second binding mixtures, wherein a test compound which reduces the binding in the second binding mixture as compared to the first binding mixture is identified as a potential inhibitor of papillomavirus episome replication.

* * * * *

REEXAMINATION CERTIFICATE (4088th)

United States Patent [19]
Howley et al.

[11] B1 5,821,048
[45] Certificate Issued May 23, 2000

[54] METHODS, KITS, AND COMPOSITIONS FOR DIAGNOSING PAPILLOMAVIRUS INFECTION

[75] Inventors: Peter M. Howley, Wellesley; John D. Benson, Brookline; Toshiharu Yasugi, Brookline; Hiroyuki Sakai, Brookline, all of Mass.

[73] Assignee: President and Fellows of Harvard College, Cambridge, Mass.

Reexamination Request:
No. 90/005,362, May 17, 1999

Reexamination Certificate for:
Patent No.: 5,821,048
Issued: Oct. 13, 1998
Appl. No.: 08/472,666
Filed: Jun. 7, 1995

[51] Int. Cl.[7] .............................. C12Q 1/70; C12Q 1/68; A01N 37/18; C07K 1/00

[52] U.S. Cl. ................................ 435/5; 435/6; 435/235.1; 514/2; 530/350

[58] Field of Search ................................ 435/5, 6, 235.1; 530/350; 514/2

[56] References Cited

FOREIGN PATENT DOCUMENTS

WO 93/06485  4/1993  WIPO .
WO 93/07299  4/1993  WIPO .

OTHER PUBLICATIONS

Shamanin et al. (1994) *Journal of General Virology* 75:1149–1156.

*Primary Examiner*—Cecilia Tsang

[57] ABSTRACT

Methods, kits, and compositions are provided for diagnosing papillomavirus infections by detecting the interaction between a papillomavirus E1 protein interaction domain and a papillomavirus E2 protein interaction domain.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–3 is confirmed.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 605 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bovine papillomavirus E1
        ( B ) STRAIN: BPV-1

( x i ) SEQUENCE DESCRIPTION: SEQ ID NO:1:

```
Met  Ala  Asn  Asp  Lys  Gly  Ser  Asn  Trp  Asp  Ser  Gly  Leu  Gly  Cys  Ser
 1               5                        10                       15

Tyr  Leu  Leu  Thr  Glu  Ala  Glu  Cys  Glu  Ser  Asp  Lys  Glu  Asn  Glu  Glu
               20                       25                       30

Pro  Gly  Ala  Gly  Val  Glu  Leu  Ser  Val  Glu  Ser  Asp  Arg  Tyr  Asp  Ser
               35                       40                       45

Gln  Asp  Glu  Asp  Phe  Val  Asp  Asn  Ala  Ser  Val  Phe  Gln  Gly  Asn  His
          50                       55                       60

Leu  Glu  Val  Phe  Gln  Ala  Leu  Glu  Lys  Lys  Ala  Gly  Glu  Glu  Gln  Ile
 65                       70                       75                       80
```

| | | | | | | | | | | | | | | |
|---|---|---|---|---|---|---|---|---|---|---|---|---|---|---|
| Leu | Asn | Leu | Lys | Arg 85 | Lys | Val | Leu | Gly 90 | Ser | Gln | Asn | Ser | Ser 95 | Gly |
| Ser | Glu | Ala | Ser 100 | Glu | Thr | Pro | Val | Lys 105 | Arg | Arg | Lys | Ser | Gly 110 | Ala | Lys |
| Arg | Arg | Leu 115 | Phe | Ala | Glu | Asn | Glu 120 | Ala | Asn | Arg | Val | Leu 125 | Thr | Pro | Leu |
| Gln | Val 130 | Gln | Gly | Glu | Gly | Glu 135 | Gly | Arg | Gln | Glu | Leu 140 | Asn | Glu | Gln |
| Ala 145 | Ile | Ser | His | Leu | His 150 | Leu | Gln | Leu | Val | Lys 155 | Ser | Lys | Asn | Ala | Thr 160 |
| Val | Phe | Lys | Leu | Gly 165 | Leu | Phe | Lys | Ser | Leu 170 | Phe | Leu | Cys | Ser | Phe 175 | His |
| Asp | Ile | Thr | Arg 180 | Leu | Phe | Lys | Asn | Asp 185 | Lys | Thr | Thr | Asn | Gln 190 | Gln | Trp |
| Val | Leu | Ala 195 | Val | Phe | Gly | Leu | Ala 200 | Glu | Val | Phe | Phe 205 | Glu | Ala | Ser | Phe |
| Glu | Leu 210 | Leu | Lys | Lys | Gln | Cys 215 | Ser | Phe | Leu | Gln | Met 220 | Gln | Lys | Arg | Ser |
| His 225 | Glu | Gly | Gly | Thr | Cys 230 | Ala | Val | Tyr | Leu | Ile 235 | Cys | Phe | Asn | Thr | Ala 240 |
| Lys | Ser | Arg | Glu | Thr 245 | Val | Arg | Asn | Leu | Met 250 | Ala | Asn | Thr | Leu | Asn 255 | Val |
| Arg | Glu | Glu | Cys 260 | Leu | Met | Leu | Gln | Pro 265 | Ala | Lys | Ile | Arg | Gly 270 | Leu | Ser |
| Ala | Ala | Leu 275 | Phe | Trp | Phe | Lys | Ser 280 | Ser | Leu | Ser | Pro | Ala 285 | Thr | Leu | Lys |
| His | Gly 290 | Ala | Leu | Pro | Glu | Trp 295 | Ile | Arg | Ala | Gln | Thr 300 | Thr | Leu | Asn | Glu |
| Ser 305 | Leu | Gln | Thr | Glu | Lys 310 | Phe | Asp | Phe | Gly | Thr 315 | Met | Val | Gln | Trp | Ala 320 |
| Tyr | Asp | His | Lys | Tyr 325 | Ala | Glu | Glu | Ser | Lys 330 | Ile | Ala | Tyr | Glu | Tyr 335 | Ala |
| Leu | Ala | Ala | Gly 340 | Ser | Asp | Ser | Asn | Ala 345 | Arg | Ala | Phe | Leu | Ala 350 | Thr | Asn |
| Ser | Gln | Ala | Lys 355 | His | Val | Lys | Asp | Cys 360 | Ala | Thr | Met | Val | Arg 365 | His | Tyr |
| Leu | Arg | Ala 370 | Glu | Thr | Gln | Ala 375 | Leu | Ser | Met | Pro | Ala 380 | Tyr | Ile | Lys | Ala |
| Arg 385 | Cys | Lys | Leu | Ala | Thr 390 | Gly | Glu | Gly | Ser | Trp 395 | Lys | Ser | Ile | Leu | Thr 400 |
| Phe | Phe | Asn | Tyr | Gln 405 | Asn | Ile | Glu | Leu | Ile 410 | Thr | Phe | Ile | Asn | Ala 415 | Leu |
| Lys | Leu | Trp | Leu 420 | Lys | Gly | Ile | Pro | Lys 425 | Lys | Asn | Cys | Leu | Ala 430 | Phe | Ile |
| Gly | Pro | Pro | Asn 435 | Thr | Gly | Lys | Ser | Met 440 | Leu | Cys | Asn | Ser | Leu 445 | Ile | His |
| Phe | Leu 450 | Gly | Gly | Ser | Val | Leu 455 | Ser | Phe | Ala | Asn | His 460 | Lys | Ser | His | Phe |
| Trp 465 | Leu | Ala | Ser | Leu | Ala 470 | Asp | Thr | Arg | Ala | Ala 475 | Leu | Val | Asp | Asp | Ala 480 |
| Thr | His | Ala | Cys | Trp 485 | Arg | Tyr | Phe | Asp | Thr 490 | Tyr | Leu | Arg | Asn | Ala 495 | Leu |
| Asp | Gly | Tyr | Pro 500 | Val | Ser | Ile | Asp | Arg 505 | Lys | His | Lys | Ala | Ala 510 | Val | Gln |

```
        Ile  Lys  Ala  Pro  Pro  Leu  Leu  Val  Thr  Ser  Asn  Ile  Asp  Val  Gln  Ala
             515                520                     525

Glu  Asp  Arg  Tyr  Leu  Tyr  Leu  His  Ser  Arg  Val  Gln  Thr  Phe  Arg  Phe
             530                535                     540

Glu  Gln  Pro  Cys  Thr  Asp  Glu  Ser  Gly  Glu  Gln  Pro  Phe  Asn  Ile  Thr
        545                     550                     555                          560

Asp  Ala  Asp  Trp  Lys  Ser  Phe  Phe  Val  Arg  Leu  Trp  Gly  Arg  Leu  Asp
                            565                     570                     575

Leu  Ile  Asp  Glu  Glu  Glu  Asp  Ser  Glu  Glu  Asp  Gly  Asp  Ser  Met  Arg
                       580                     585                     590

Thr  Phe  Thr  Cys  Ser  Ala  Arg  Asn  Thr  Asn  Ala  Val  Asp
             595                          600                     605
```

( 2 ) INFORMATION FOR SEQ ID NO:2:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bovine papillomavirus E2
        ( B ) STRAIN: BPV-1

( x i ) SEQUENCE DESCRIPTION: SEQ ID NO:2:

```
        Met  Glu  Thr  Ala  Cys  Glu  Arg  Leu  His  Val  Ala  Gln  Glu  Thr  Gln  Met
        1                    5                        10                          15

Gln  Leu  Ile  Glu  Lys  Ser  Ser  Asp  Lys  Leu  Gln  Asp  His  Ile  Leu  Tyr
                       20                     25                          30

Trp  Thr  Ala  Val  Arg  Thr  Glu  Asn  Thr  Leu  Leu  Ser  Ala  Ala  Arg  Lys
                  35                     40                          45

Lys  Gly  Val  Thr  Val  Leu  Gly  His  Cys  Arg  Val  Pro  His  Ser  Val  Val
             50                          55                     60

Cys  Gln  Glu  Arg  Ala  Lys  Gln  Ala  Ile  Glu  Met  Gln  Leu  Ser  Leu  Gln
        65                       70                     75                          80

Glu  Leu  Ser  Lys  Thr  Glu  Phe  Gly  Asp  Glu  Pro  Trp  Ser  Leu  Leu  Asp
                            85                     90                          95

Thr  Ser  Trp  Asp  Arg  Tyr  Met  Ser  Glu  Pro  Lys  Arg  Cys  Phe  Lys  Lys
                       100                    105                         110

Gly  Ala  Arg  Val  Val  Glu  Val  Glu  Phe  Asp  Gly  Asn  Ala  Ser  Asn  Thr
                  115                         120                         125

Asn  Trp  Tyr  Thr  Val  Tyr  Ser  Asn  Leu  Tyr  Met  Arg  Thr  Glu  Asp  Gly
             130                         135                    140

Trp  Gln  Leu  Ala  Lys  Ala  Gly  Ala  Asp  Gly  Thr  Gly  Leu  Tyr  Tyr  Cys
        145                         150                         155                    160

Thr  Met  Ala  Gly  Ala  Gly  Arg  Ile  Tyr  Tyr  Ser  Arg  Phe  Gly  Asp  Glu
                            165                         170                         175

Ala  Ala  Arg  Phe  Ser  Thr  Thr  Gly  His  Tyr  Ser  Val  Arg  Asp  Gln  Asp
                       180                         185                    190

Arg  Val  Tyr  Ala  Gly  Val  Ser  Ser  Thr  Ser  Ser  Asp  Phe  Arg  Asp  Arg
                  195                         200                    205

Pro  Asp  Gly  Val  Trp  Val  Ala  Ser  Glu  Gly  Pro  Glu  Gly  Asp  Pro  Ala
             210                         215                    220

Gly  Lys  Glu  Ala  Glu  Pro  Ala  Gln  Pro  Val  Ser  Ser  Leu  Leu  Gly  Ser
        225                         230                    235                         240
```

```
Pro  Ala  Cys  Gly  Pro  Ile  Arg  Ala  Gly  Leu  Gly  Trp  Val  Arg  Asp  Gly
               245                      250                           255

Pro  Arg  Ser  His  Pro  Tyr  Asn  Phe  Pro  Ala  Gly  Ser  Gly  Gly  Ser  Ile
               260                      265                     270

Leu  Arg  Ser  Ser  Ser  Thr  Pro  Val  Gln  Gly  Thr  Val  Pro  Val  Asp  Leu
          275                      280                     285

Ala  Ser  Arg  Gln  Glu  Glu  Glu  Gln  Ser  Pro  Asp  Ser  Thr  Glu  Glu
290                           295                     300

Glu  Pro  Val  Thr  Leu  Pro  Arg  Arg  Thr  Thr  Asn  Asp  Gly  Phe  His  Leu
305                      310                      315                           320

Leu  Lys  Ala  Gly  Gly  Ser  Cys  Phe  Ala  Leu  Ile  Ser  Gly  Thr  Ala  Asn
                    325                      330                           335

Gln  Val  Lys  Cys  Tyr  Arg  Phe  Arg  Val  Lys  Lys  Asn  His  Arg  His  Arg
               340                      345                     350

Tyr  Glu  Asn  Cys  Thr  Thr  Thr  Trp  Phe  Thr  Val  Ala  Asp  Asn  Gly  Ala
               355                      360                     365

Glu  Arg  Gln  Gly  Gln  Ala  Gln  Ile  Leu  Ile  Thr  Phe  Gly  Ser  Pro  Ser
     370                      375                     380

Gln  Arg  Gln  Asp  Phe  Leu  Lys  His  Val  Pro  Leu  Pro  Pro  Gly  Met  Asn
385                      390                      395                           400

Ile  Ser  Gly  Phe  Thr  Ala  Ser  Leu  Asp  Phe
               405                      410
```

( 2 ) INFORMATION FOR SEQ ID NO:3:

( i ) SEQUENCE CHARACTERISTICS:
        ( A ) LENGTH: 649 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Human papillomavirus- 16 E1
        ( B ) STRAIN: HPV-16

( x i ) SEQUENCE DESCRIPTION: SEQ ID NO:3:

```
Met  Ala  Asp  Pro  Ala  Gly  Thr  Asn  Gly  Glu  Glu  Gly  Thr  Gly  Cys  Asn
1               5                        10                          15

Gly  Trp  Phe  Tyr  Val  Glu  Ala  Val  Glu  Lys  Lys  Thr  Gly  Asp  Ala
               20                       25                      30

Ile  Ser  Asp  Asp  Glu  Asn  Glu  Asn  Asp  Ser  Asp  Thr  Gly  Glu  Asp  Leu
          35                        40                      45

Val  Asp  Phe  Ile  Val  Asn  Asp  Asn  Asp  Tyr  Leu  Thr  Gln  Ala  Glu  Thr
     50                        55                      60

Glu  Thr  Ala  His  Ala  Leu  Phe  Thr  Ala  Gln  Glu  Ala  Lys  Gln  His  Arg
65                       70                      75                           80

Asp  Ala  Val  Gln  Val  Leu  Lys  Arg  Lys  Tyr  Leu  Val  Ser  Pro  Leu  Ser
               85                       90                      95

Asp  Ile  Ser  Gly  Cys  Val  Asp  Asn  Asn  Ile  Ser  Pro  Arg  Leu  Lys  Ala
               100                      105                     110

Ile  Cys  Ile  Glu  Lys  Gln  Ser  Arg  Ala  Ala  Lys  Arg  Arg  Leu  Phe  Glu
          115                      120                     125

Ser  Glu  Asp  Ser  Gly  Tyr  Gly  Asn  Thr  Glu  Val  Glu  Thr  Gln  Gln  Met
     130                      135                     140

Leu  Gln  Val  Glu  Gly  Arg  His  Glu  Thr  Glu  Thr  Pro  Cys  Ser  Gln  Tyr
145                      150                      155                          160

Ser  Gly  Gly  Ser  Gly  Gly  Gly  Cys  Ser  Gln  Tyr  Ser  Ser  Gly  Ser  Gly
```

```
                              165                          170                         175
        Gly  Glu  Gly  Val  Ser  Glu  Arg  His  Thr  Ile  Cys  Gln  Thr  Pro  Leu  Thr
                            180                     185                      190

Asn  Ile  Leu  Asn  Val  Leu  Lys  Thr  Ser  Asn  Ala  Lys  Ala  Ala  Met  Leu
                       195                      200                 205

Ala  Lys  Phe  Lys  Glu  Leu  Tyr  Gly  Val  Ser  Phe  Ser  Glu  Leu  Val  Arg
                  210                      215                      220

Pro  Phe  Lys  Ser  Asn  Lys  Ser  Thr  Cys  Cys  Asp  Trp  Cys  Ile  Ala  Ala
        225                      230                      235                      240

Phe  Gly  Leu  Thr  Pro  Ser  Ile  Ala  Asp  Ser  Ile  Lys  Thr  Leu  Leu  Gln
                            245                      250                      255

Gln  Tyr  Cys  Leu  Tyr  Leu  His  Ile  Gln  Ser  Leu  Ala  Cys  Ser  Trp  Gly
                       260                      265                 270

Met  Val  Val  Leu  Leu  Leu  Val  Arg  Tyr  Lys  Cys  Gly  Lys  Asn  Arg  Glu
                  275                      280                 285

Thr  Ile  Glu  Lys  Leu  Leu  Ser  Lys  Leu  Leu  Cys  Val  Ser  Pro  Met  Cys
             290                      295                 300

Met  Met  Ile  Glu  Pro  Pro  Lys  Leu  Arg  Ser  Thr  Ala  Ala  Ala  Leu  Tyr
        305                      310                      315                      320

Trp  Tyr  Lys  Thr  Gly  Ile  Ser  Asn  Ile  Ser  Glu  Val  Tyr  Gly  Asp  Thr
                            325                      330                 335

Pro  Glu  Trp  Ile  Gln  Arg  Gln  Thr  Val  Leu  Gln  His  Ser  Phe  Asn  Asp
                       340                      345                 350

Cys  Thr  Phe  Glu  Leu  Ser  Gln  Met  Val  Gln  Trp  Ala  Tyr  Asp  Asn  Asp
                  355                      360                 365

Ile  Val  Asp  Asp  Ser  Glu  Ile  Ala  Tyr  Lys  Tyr  Ala  Gln  Leu  Ala  Asp
             370                      375                 380

Thr  Asn  Ser  Asn  Ala  Ser  Ala  Phe  Leu  Lys  Ser  Asn  Ser  Gln  Ala  Lys
        385                      390                 395                      400

Ile  Val  Lys  Asp  Cys  Ala  Thr  Met  Cys  Arg  His  Tyr  Lys  Arg  Ala  Glu
                            405                      410                 415

Lys  Lys  Gln  Met  Ser  Met  Ser  Gln  Trp  Ile  Lys  Tyr  Arg  Cys  Asp  Arg
                       420                      425                 430

Val  Asp  Asp  Gly  Gly  Asp  Trp  Lys  Gln  Ile  Val  Met  Phe  Leu  Arg  Tyr
                  435                      440                 445

Gln  Gly  Val  Glu  Phe  Met  Ser  Phe  Leu  Thr  Ala  Leu  Lys  Arg  Phe  Leu
             450                      455                 460

Gln  Gly  Ile  Pro  Lys  Lys  Asn  Cys  Ile  Leu  Leu  Tyr  Gly  Ala  Ala  Asn
        465                      470                      475                      480

Thr  Gly  Lys  Ser  Leu  Phe  Gly  Met  Ser  Leu  Met  Lys  Phe  Leu  Gln  Gly
                            485                      490                 495

Ser  Val  Ile  Cys  Phe  Val  Asn  Ser  Lys  Ser  His  Phe  Trp  Leu  Gln  Pro
                       500                      505                 510

Leu  Ala  Asp  Ala  Lys  Ile  Gly  Met  Leu  Asp  Asp  Ala  Thr  Val  Pro  Cys
                  515                      520                 525

Trp  Asn  Tyr  Ile  Asp  Asp  Asn  Leu  Arg  Asn  Ala  Leu  Asp  Gly  Asn  Leu
             530                      535                 540

Val  Ser  Met  Asp  Val  Lys  His  Arg  Pro  Leu  Val  Gln  Leu  Lys  Cys  Pro
        545                      550                      555                      560

Pro  Leu  Leu  Ile  Thr  Ser  Asn  Ile  Asn  Ala  Gly  Thr  Asp  Ser  Arg  Trp
                            565                      570                 575

Pro  Tyr  Leu  His  Asn  Arg  Leu  Val  Val  Phe  Thr  Phe  Pro  Asn  Glu  Phe
                       580                      585                 590
```

| Pro | Phe | Asp | Glu | Asn | Gly | Asn | Pro | Val | Tyr | Glu | Leu | Asn | Asp | Lys | Asn |
| | | 595 | | | | | 600 | | | | | 605 | | | |

| Trp | Lys | Ser | Phe | Phe | Ser | Arg | Thr | Trp | Ser | Arg | Leu | Ser | Leu | His | Glu |
| | 610 | | | | | 615 | | | | | 620 | | | | |

| Asp | Glu | Asp | Lys | Glu | Asn | Gly | Asp | Ser | Leu | Pro | Thr | Phe | Lys | Cys |
| 625 | | | | | 630 | | | | 635 | | | | | 640 |

| Val | Ser | Gly | Gln | Asn | Thr | Asn | Thr | Leu |
| | | | | 645 | | | | |

( 2 ) INFORMATION FOR SEQ ID NO:4:

( i ) SEQUENCE CHARACTERISTICS:
( A ) LENGTH: 365 amino acids
( B ) TYPE: amino acid
( D ) TOPOLOGY: linear ( i i ) MOLECULE TYPE: protein ( v i ) ORIGINAL SOURCE:
( A ) ORGANISM: Human papillomavirus- 16 E2
( B ) STRAIN: HPV-16 E2

( x i ) SEQUENCE DESCRIPTION: SEQ ID NO:4:

| Met | Glu | Thr | Leu | Cys | Gln | Arg | Leu | Asn | Val | Cys | Gln | Asp | Lys | Ile | Leu |
| 1 | | | | 5 | | | | | 10 | | | | | 15 | |

| Thr | His | Tyr | Glu | Asn | Asp | Ser | Thr | Asp | Leu | Arg | Asp | His | Ile | Asp | Tyr |
| | | | 20 | | | | | 25 | | | | | 30 | | |

| Trp | Lys | His | Met | Arg | Leu | Glu | Cys | Ala | Ile | Tyr | Tyr | Lys | Ala | Arg | Glu |
| | | 35 | | | | | 40 | | | | | 45 | | | |

| Met | Gly | Phe | Lys | His | Ile | Asn | His | Gln | Val | Val | Pro | Thr | Leu | Ala | Val |
| | 50 | | | | | 55 | | | | | 60 | | | | |

| Ser | Lys | Asn | Lys | Ala | Leu | Gln | Ala | Ile | Glu | Leu | Gln | Leu | Thr | Leu | Glu |
| 65 | | | | | 70 | | | | | 75 | | | | | 80 |

| Thr | Ile | Tyr | Asn | Ser | Gln | Tyr | Ser | Asn | Glu | Lys | Trp | Thr | Leu | Gln | Asp |
| | | | | 85 | | | | | 90 | | | | | 95 | |

| Val | Ser | Leu | Glu | Val | Tyr | Leu | Thr | Ala | Pro | Thr | Gly | Cys | Ile | Lys | Lys |
| | | | 100 | | | | | 105 | | | | | 110 | | |

| His | Gly | Tyr | Thr | Val | Glu | Val | Gln | Phe | Asp | Gly | Asp | Ile | Cys | Asn | Thr |
| | | 115 | | | | | 120 | | | | | 125 | | | |

| Met | His | Tyr | Thr | Asn | Trp | Thr | His | Ile | Tyr | Ile | Cys | Glu | Glu | Ala | Ser |
| | 130 | | | | | 135 | | | | | 140 | | | | |

| Val | Thr | Val | Val | Glu | Gly | Gln | Val | Asp | Tyr | Tyr | Gly | Leu | Tyr | Tyr | Val |
| 145 | | | | | 150 | | | | | 155 | | | | | 160 |

| His | Glu | Gly | Ile | Arg | Thr | Tyr | Phe | Val | Gln | Phe | Lys | Asp | Asp | Ala | Glu |
| | | | | 165 | | | | | 170 | | | | | 175 | |

| Lys | Tyr | Ser | Lys | Asn | Lys | Val | Trp | Glu | Val | His | Ala | Gly | Gly | Gln | Val |
| | | | 180 | | | | | 185 | | | | | 190 | | |

| Ile | Leu | Cys | Pro | Thr | Ser | Val | Phe | Ser | Ser | Asn | Glu | Val | Ser | Ser | Pro |
| | | 195 | | | | | 200 | | | | | 205 | | | |

| Glu | Ile | Ile | Arg | Gln | His | Leu | Ala | Asn | His | Pro | Ala | Ala | Thr | His | Thr |
| | 210 | | | | | 215 | | | | | 220 | | | | |

| Lys | Ala | Val | Ala | Leu | Gly | Thr | Glu | Glu | Thr | Gln | Thr | Thr | Ile | Gln | Arg |
| 225 | | | | | 230 | | | | | 235 | | | | | 240 |

| Pro | Arg | Ser | Glu | Pro | Asp | Thr | Gly | Asn | Pro | Cys | His | Thr | Thr | Lys | Leu |
| | | | | 245 | | | | | 250 | | | | | 255 | |

| Leu | His | Arg | Asp | Ser | Val | Asp | Ser | Ala | Pro | Ile | Leu | Thr | Ala | Phe | Asn |
| | | | 260 | | | | | 265 | | | | | 270 | | |

| Ser | Ser | His | Lys | Gly | Arg | Ile | Asn | Cys | Asn | Ser | Asn | Thr | Thr | Pro | Ile |

|   |   |   | 275 |   |   |   | 280 |   |   |   | 285 |   |   |   |
|---|---|---|---|---|---|---|---|---|---|---|---|---|---|---|
| Val | His | Leu | Lys | Gly | Asp | Ala | Asn | Thr | Leu | Lys | Cys | Leu | Arg | Tyr | Arg |
|  | 290 |  |  |  |  | 295 |  |  |  |  | 300 |  |  |  |  |
| Phe | Lys | Lys | His | Cys | Thr | Leu | Tyr | Thr | Ala | Val | Ser | Ser | Thr | Trp | His |
| 305 |  |  |  |  | 310 |  |  |  |  | 315 |  |  |  |  | 320 |
| Trp | Thr | Gly | His | Asn | Val | Lys | His | Lys | Ser | Ala | Ile | Val | Thr | Leu | Thr |
|  |  |  |  | 325 |  |  |  |  | 330 |  |  |  |  | 335 |  |
| Tyr | Asp | Ser | Glu | Trp | Gln | Arg | Asp | Gln | Phe | Leu | Ser | Gln | Val | Lys | Ile |
|  |  |  | 340 |  |  |  |  | 345 |  |  |  |  | 350 |  |  |
| Pro | Lys | Thr | Ile | Thr | Val | Ser | Thr | Gly | Phe | Met | Ser | Ile |  |  |  |
|  |  | 355 |  |  |  |  | 360 |  |  |  |  | 365 |  |  |  |